(12) United States Patent
Gao et al.

(10) Patent No.: US 8,017,031 B2
(45) Date of Patent: Sep. 13, 2011

(54) BIOCOMPATIBLE MAGNETIC NANOCRYSTAL, POWDER OF A BIOCOMPATIBLE MAGNETIC NANOCRYSTAL BEARING A SURFACE REACTIVE GROUP AND PREPARATIONS THEREOF

(75) Inventors: Mingyuan Gao, Beijing (CN); Fengqin Hu, Beijing (CN); Shujie Liu, Beijing (CN); Xianyong Lu, Beijing (CN)

(73) Assignee: Institute of Chemistry, Chinese Academy of Sciences, Beijing (CN)

( * ) Notice: Subject to any disclaimer, the term of this patent is extended or adjusted under 35 U.S.C. 154(b) by 738 days.

(21) Appl. No.: 12/008,864

(22) Filed: Jan. 14, 2008

(65) Prior Publication Data
US 2008/0203351 A1 Aug. 28, 2008

(30) Foreign Application Priority Data

| Jan. 15, 2007 | (CN) | ............................. | 2007 1 0062721 |
| Apr. 5, 2007 | (CN) | ............................. | 2007 1 0065163 |
| Nov. 15, 2007 | (CN) | ............................. | 2007 1 0187270 |
| Nov. 15, 2007 | (CN) | ............................. | 2007 1 0187275 |

(51) Int. Cl.
*H01F 1/33* (2006.01)
(52) U.S. Cl. .................................. 252/62.52; 252/62.54
(58) Field of Classification Search .............. 252/62.52, 252/62.54
See application file for complete search history.

(56) References Cited

U.S. PATENT DOCUMENTS

| 6,767,635 | B1 * | 7/2004 | Bahr et al. | ..................... 428/402 |
| 2005/0265922 | A1 * | 12/2005 | Nie et al. | ..................... 424/1.11 |
| 2007/0116955 | A1 * | 5/2007 | Chen et al. | ..................... 428/403 |

FOREIGN PATENT DOCUMENTS

| CN | 03136273 | 12/2003 |
| CN | 03136273.7 | 12/2003 |
| CN | 03136275 | 11/2004 |
| CN | 03136275.3 | 11/2004 |
| CN | 200610114459.X | 5/2008 |

OTHER PUBLICATIONS

Li et al, "One-Pot reaction to Synthesize Biocompatible Magnetite naoparticles", Adv. Mater. vol. 17, No. 8, Apr. 18, 2005, pp. 1001-1005.*
Hu et al, "Preparation of Biocompatable Magnetite Naoacrystals for In Vivo Magnetic Resonance Dectection of Cancer"<Adv. Mater. vol. 18, Sep. 14, 2006, pp. 2553-2556.*
Hermanson, Bioconjugate Techniques, Academic Press, New York, 1996, pp. 173-176.

Hu et al., "Preparation of Biocompatible Magnetite Nanocrystals for in Vivo Magnetic Resonance Detection of Cancer," Adv. Mater. (2006) 18(19):2553-2556.
Hu et al., "Preparation of magnetic nanocrystals with surface reactive moieties by one-pot reaction," J. Colloid and Interface Science (2007) 311(2):469-474.
Hyeon et al., "Synthesis of Highly Crystalline and Monodisperse Maghemite Nanocrystallites without a Size-Selection Process," J. Am. Chem. Soc. (2001) 123:12798-12801.
Jana et al., "Size- and Shape-Controlled Magnetic (Cr, Mn, Fe, Co, Ni) Oxide Nanocrystals via a Simple and General Approach," Chem. Mater. (2004) 16:3931-3935.
Li et al., "One-Pot Reaction to Synthesize Biocompatible Magnetite Particles," Adv. Mater. (2005) 17(8):1001-1005.
Li et al., "Preparation of Water-Soluble Magnetic Nanocrystals from Hydrated Ferric Salts in 2-Pyrrolidone: Mechanism Leading to $Fe_3O_4$," Angew. Chem. Int. Ed. (2005) 44:123-126.
Li et al., "One-Pot Reaction to Synthesize Water-Soluble Magnetite Nanocrystals," Chem. Mater. (2004) 16:1391-1393.
Niu et al., "Amphiphilic ABC Triblock Copolymer-Assisted Synthesis of Core/Shell Structured CdTe Nanowires," Langmuir (2005) 21(9):4205-4210.
Park et al., "Ultra-large-scale syntheses of monodisperse nanocrystals," Nature Materials (2004) 3(12):891-895.
Popov and Wendlandt, "Cupferron and Neocupferron Complexes of the Rare Earth Elements," Anal. Chem. (1954) 26(5):883-886.
Rockenberger et al., "A New Nonhydrolytic Single-Precursor Approach to Surfactant-Capped Nanocrystals of Transition Metal Oxides," J. Am. Chem. Soc. (1999) 121:1159511596.
Sun et al., "Size-Controlled Synthesis of Magnetite Nanoparticles," J. Am. Chem. Soc. (2002) 124:8204-8205.
Yu et al., "Synthesis of of Poly (ō-Carpolactone)/Poly(Ethylene Glycol) Block Copolymers and Surface Property Control of Their Microspheres," Acta Polymerica Sinica (2006) 5:740-744 (with English Abstract).

* cited by examiner

*Primary Examiner* — C. Melissa Koslow
(74) *Attorney, Agent, or Firm* — Morrison & Foerster LLP

(57) ABSTRACT

This invention is concerned with biocompatible magnetic nanocrystals highly soluble and dispersible in a physiological buffer, powder of biocompatible magnetic nanocrystals and nanocrystals bearing surface reactive N-hydroxysuccinimide ester moiety, and preparations thereof. The magnetic nanocrystals in powder form are highly soluble in a physiological buffer. The resultant aqueous colloidal solution presents long term stability in ambient conditions. Moreover, the carboxyl group on the surface of the magnetic nanocrystals can be converted to N-hydroxysuccinimide ester moiety in an organic solvent. The resultant powder of the magnetic nanocrystals carrying surface N-hydroxysuccinimide ester moiety is soluble and dispersible in an aqueous solution. Different types of biomolecules bearing amino group can covalently be attached to the magnetic nanocrystal simply by mixing them in aqueous solutions. Moreover, the powder of the magnetic nanocrystals bearing surface N-hydroxysuccinimide ester moiety retain reaction activity with biomolecule after long-term storage.

14 Claims, 9 Drawing Sheets

BIOCOMPATIBLE MAGNETIC NANOCRYSTAL, POWDER OF A BIOCOMPATIBLE MAGNETIC NANOCRYSTAL BEARING A SURFACE REACTIVE GROUP AND PREPARATIONS THEREOF

CROSS-REFERENCE TO RELATED APPLICATIONS

This application claims priority from China patent application No. 200710062721.5 filed Jan. 15, 2007; China patent application No. 200710065163.8 filed Apr. 5, 2007; China patent application No. 200710187270.8 filed Nov. 15, 2007; and China patent application No. 200710187275.0 filed Nov. 15, 2007. The contents of the above-referenced applications are incorporated herein by this reference in their entirety.

TECHNICAL FIELD

This invention relates to biocompatible magnetic nanocrystals highly soluble and stably dispersible in physiological buffer, powders of biocompatible magnetic nanocrystals and biocompatible magnetic nanocrystals bearing surface reactive N-hydroxysuccinimide ester moiety, and preparations thereof.

BACKGROUND

Magnetic nanocrystals are widely used in different types of biological applications such as DNA/RNA, protein, and cell separation and purification, and biomedical applications such as magnetic resonance imaging (MRI), hypothermia treatment of cancer, and drug delivery, etc. However, the biocompatibility, surface functionality, chemical stability, and colloidal stability of the magnetic nanocrystals under physiological conditions remain the bottlenecks for the abovementioned applications.

At present, the chemical synthetic methods for magnetic nanocrystals and nanoparticles mainly rely on hydrolysis or pyrolysis of metal compounds, such as (co)precipitation method, thermal-decomposition method, microemulsion method, sonochemical method, and so on. The nanoparticles prepared by (co)precipitation method have a wide particle size distribution and less-defined composition; the nanoparticles prepared by microemulsion method show low crystallinity degree and weak magnetic responsivity; the sonochemical method shows poor ability in controlling the size and the morphology of the resultant nanoparticles. However, thermal-decomposition method developed recently has successfully overcome the above-mentioned problems. As higher reaction temperature are usually adopted in the thermal decomposition method, the nucleation process, growth process and the crystallinity degree of the resultant nanocrystals can better be controlled. On the other hand, the use of non-polar or weak polar organic compound as reaction medium can prevent water from being involved in the reaction, which is greatly helpful for defining the composition of the resultant nanocrystals. From the following literatures, i.e., Rockenberger J, Scher E C, Alivisatos A P. A New Nonhydrolytic Single-Precursor Approach to Surfactant-Capped Nanocrystals of Transition Metal Oxides. *J. Am. Chem. Soc.* 1999, 121(49): 11595-11596; Jana N R, Chen Y, Peng X. Size- and Shape-Controlled Magnetic (Cr, Mn, Fe, Co, Ni) Oxide Nanocrystals via a Simple and General Approach. *Chem. Mater.* 2004, 16(20): 3931-3935; Park J, An K J, Hwang Y S, Park J G, Noh H J, et al. Ultra-large-scale syntheses of monodisperse nanocrystals. *Nature Materials* 2004, 3(12): 891-895; Hyeon T, Lee S S, Park J, Chung Y, Bin Na H. Synthesis of highly crystalline and monodisperse maghemite nanocrystallites without a size-selection process. *J. Am. Chem. Soc.* 2001, 123(51): 12798-12801; Sun S H, Zeng H. Size-controlled synthesis of magnetite nanoparticles. *J. Am. Chem. Soc.* 2002 124(28): 8204-8205, it can be found out that the solvent for preparing high-quality magnetic iron oxide particles is typically chosen from non-polar and weak polar organic compounds with a high boiling point. In addition, small molecules such as fatty acids, fatty amines or fatty alcohols are typically presented in the reaction system. The above-mentioned investigations have formed a solid basis for preparing high quality magnetic nanocrystals. However, the direct products of the above mentioned preparations involving thermal decomposition method are typically characterized by a satisfying organic dissolvability due to the hydrophobic surface modification by small alkyl molecules. Therefore, it is impossible to directly use them at single particle level for in vivo applications. Although the hydrophobic magnetic nanocrystals can be transferred into an aqueous solution via a ligand-exchange process, the post-preparative procedures are very complicated and laborious.

Recently, Mingyuan Gao's group from the Institute of Chemistry, Chinese Academy of Sciences further developed the thermal-decomposition method by adopting high boiling point strong-polar solvent as reaction medium as well as a coordinating solvent and established a one-pot reaction technique for producing water soluble magnetic nanocrystals (Chinese patent: 03136275.3 and 200610114459.X). In their technique, the weak polar and non-polar solvents were replaced by a strong polar solvent such as 2-pyrrolidone. For example, by pyrolyzing ferric triacetylacetonate (Li Z, Chen H, Bao H B, Gao M Y. One-pot reaction to synthesize water-soluble magnetite nanocrystals. *Chem. Mater.*, 2004, 16(8): 1391-1393) or $FeCl_3 \cdot H_2O$ (Li Z, Sun Q, Gao MY. Preparation of water-soluble magnetite nanocrystals from hydrated ferric salts in 2-pyrrolidone: Mechanism leading to Fe3O4. *Angew. Chem. Int. Ed.* 2005, 44(1): 123-126) in 2-pyrrolidone, they have successfully obtained water soluble magnetite nanocrystals. On the basis of these achievements, they further developed a one-pot reaction technique for producing biocompatible magnetic nanocrystals by introducing carboxyl-terminated polyethylene glycol into the reaction system (Chinese patent: 03136273.7). By this technique water soluble, biocompatible (Li Z, Wei L, Gao MY, Lei H. One-pot reaction to synthesize biocompatible magnetite nanoparticles. *Adv. Mater.* 2005, 17(8): 1001-1005) and biocompatible magnetic nanocrystals bearing surface reactive carboxyl group (Hu F Q, Wei L, Zhou Z, Ran Y L, Li Z, Gao M Y. Preparation of biocompatible magnetite nanocrystals for in vivo magnetic resonance detection of cancer. *Adv. Mater.* 2006, 18(19): 2553-2556) were successfully obtained by one-pot reaction. The biocompatible magnetite nanocrystals prepared by the technique described in the Chinese patent 03136273.7 present very good colloidal stability. Furthermore, the resultant biocompatible particles in powder form also present satisfying dissolvability in pure water. But their dissolvability and colloidal stability in physiological buffers remains to be improved. Therefore, on the basis of the Chinese patent 03136273.7, herein we further developed the one-pot reaction technique for producing biocompatible magnetic nanocrystals with better dissolvability and colloidal stability in physiological buffer. In comparison with the technique described in patent 03136273.7, the current invention however adopts nonpolar and weak polar solvent to replace the strong polar coordinating solvent. Moreover, small alkyl molecules which can coordinate with the metal ions on the surface of the magnetic nanocrystals are also present in the reaction system, apart from biocompatible macromolecules which can be chemically modified on the surface of the resultant nanocrystals. Consequently, the resultant biocompatible nanocrystals exhibit a much higher solubility and greatly improved colloidal stability in physiological buffers in comparison with the magnetite nanocrystals obtained by patent 03136273.7.

In addition, user-friendly techniques for chemically conjugating the biocompatible magnetic nanocrystals to biomolecules remain to be developed for further expanding the biomedical applications of the magnetic nanocrystals.

At present, there are mainly two kinds of methods for conjugating inorganic nanocrystals to biomolecules: 1) the first group of methods relies on the weak interactions such as electrostatic adsorption, hydrophobic interaction, the coordination interactions between metal ions on the magnetic nanocrystals and histidine residues on the biomolecules, and so on; 2) the second group of methods relies on covalent bonding between the reactive moieties from the surface capping agents on the magnetic nanocrystals and the reactive residues on the biomolecules. Compared with weak interactions, covalent bonding strategy leads to conjugate with higher stability and clearly defined conjugation structure.

At this moment, the EDC/Sulfo-NHS (1-Ethyl-3-(3-dimethylaminopropyl)carbodiimide/N-hydroxysulfosuccinimide sodium salt) mediated amidation reaction has widely used as a standard covalent coupling reaction. Different types of EDC and NHS(N-hydroxysuccinimide) derivatives have also been synthesized and used for this purpose (*Bioconjugate Techniques*, Academic Press, New York, (1996) p 173-176; *Adv. Mater.*, (2006) 18:2553-2556). One of the prominent advantages of this coupling method is that the conjugation reaction can be performed under mild conditions. However, the resultant N-hydroxysuccinimide ester moiety, as an intermediate product for further reacting with amino-bearing compounds, is very readily to hydrolyze. Therefore, the activation of the carboxyl group and the following conjugation reaction with amino-bearing biomolecules, mediated by EDC/Sulfo-NHS, have to be performed simultaneously or successively within a short time window. This is for many practical applications very inconvenient.

SUMMARY OF THE INVENTION

To solve the above problems, the present invention provides biocompatible magnetic nanocrystals which are highly soluble and stably dispersible in physiological buffers, stable powders of biocompatible magnetic nanocrystals and biocompatible magnetic nanocrystals bearing surface reactive N-hydroxysuccinimide ester moiety which can further react with biomolecules forming covalent conjugates after the magnetic powders are stored for up to one year, and preparations thereof.

Concretely, the invention includes following aspects:

In the first aspect, the invention provides size controllable, highly crystallized, and biocompatible magnetic nanocrystals highly soluble and stably dispersible in physiological buffer, and the preparation method thereof.

According to the first aspect of the invention, the biocompatible nanocrystal is paramagnetic, superparamagnetic or ferromagnetic.

According to the first aspect of the invention, the biocompatible magnetic nanocrystal is characterized in that the surface of the magnetic nanocrystal is bonded with a biocompatible macromolecule and an alkyl-containing molecule simultaneously, or a biocompatible macromolecule alone.

The magnetic nanocrystal is selected from a magnetic transition metal or an oxide thereof, a magnetic lanthanide oxide, and a magnetic oxide doped with transition metal or lanthanide. The biocompatible macromolecule is selected from polyethylene glycol or a block copolymer having a polyethylene glycol segment, the biocompatible macromolecule having a molecular weight of 600 to 20000 and bearing one or more carboxyl groups or amino groups. The alkyl-containing molecule is chosen from alkyl amines, alkyl carboxylic acids, and alkyl alcohols, the number of $CH_2$ units in the alkyl-containing molecule ranges from 4 to 24.

According to the first aspect of the invention, the biocompatible magnetic nanocrystal powder can be redissolved in a physiological buffer after being stored for half-year.

According to the first aspect of the invention, the resultant colloidal solution (magnetic fluid) of the biocompatible magnetic nanocrystals in the physiological buffer exhibit highly colloidal stability.

According to the first aspect of the invention, the magnetic nanocrystal can covalently linked with a biomolecule via the carboxyl or amine residue from the biocompatible molecules chemically bonded on the particle surface.

According to the first aspect of the invention, the size and morphology of the biocompatible magnetic nanocrystal can be tuned by varying the reaction conditions.

The biocompatible magnetic nanocrystals according to the first aspect are prepared by a "one-pot" reaction, wherein the preparation comprising steps of:

introducing a precursor of magnetic nanocrystal, a biocompatible macromolecule, and an alkyl-containing molecule into a non-polar or weak-polar high boiling-point solvent; purging the reaction system with inert gas to remove oxygen; and then heating the resultant solution to directly obtain a biocompatible magnetic nanocrystal, the precursor of magnetic nanocrystal is a metal-organic coordination compound, or a metal-inorganic compound comprising transition metal or rare-earth metal ion with a concentration of 0.001 to 0.2 mol/L, the biocompatible macromolecule is polyethylene glycol or a block copolymer having a polyethylene glycol segment, the biocompatible macromolecule having a molecular weight of 600 to 20000 and bearing one or more carboxyl groups or amino groups, and the concentration thereof ranging from 0.001 mol/L to 1 mol/L, the alkyl-containing molecule is chosen from an alkyl amine, an alkyl carboxylic acid, or an alkyl alcohol, the concentration of the alkyl-containing molecule ranging from 0 to 0.2 mol/L, and the number of $CH_2$ units in the alkyl molecule ranges from 4 to 24.

In the second aspect, the present invention provides a biocompatible magnetic nanocrystal bearing surface reactive N-hydroxysuccinimide ester moiety obtained by converting the surface carboxyl group to N-hydroxysuccinimide ester moiety in an organic solvent.

According to the second aspect of the invention, the powder of the biocompatible magnetic nanocrystals bearing surface reactive N-hydroxysuccinimide ester moiety can covalently conjugate to a biomolecule bearing amino group by directly mixing them in an aqueous solution. The biomolecule bearing amino group is chosen from amino acids, peptides, proteins, or derivatives of carbohydrates and nucleic acids bearing amino group.

According to the second aspect of the invention, the magnetic nanocrystal bearing surface reactive N-hydroxysuccinimide ester moiety still retains reactivity, after long-term storage in powder form, with the biomolecule bearing amino group.

The powder of biocompatible magnetic nanocrystals bearing surface reactive N-hydroxysuccinimide ester moiety according to the second aspect is prepared by the method comprising the following steps:

1) introducing an organic solution of N-hydroxysuccinimide (NHS) followed by an organic solution of dicyclohexylcarbodiimide (DCC) or N,N-diisopropylcarbodiimide (DIC) into an organic solution of the biocompatible magnetic nanocrystals bearing surface carboxyl group, to activate the surface carboxyl groups on the magnetic nanocrystals at room temperature for 40 minutes-18 hours or at 4° C. for 2 hours-24 hours, wherein the molar ratio between the magnetic nanocrystal and dicyclohexylcarbodiimide or the molar ratio between the magnetic nanocrystal and N,N-diisopropylcarbodiimide ranges from 1:2 to 1:2000, and the molar ratio between dicyclohexylcarbodiimide and N-hydroxysuccinimide or between N,N-diisopropylcarbodiimide and N-hydroxysuccinimide ranges from 1:0.9 to 1:10; or introducing the organic solution of dicyclohexylcarbodiimide or N,N-diisopropylcarbodiimide dropwise into an organic solution containing both magnetic nanocrystals bearing surface carboxyl group and N-hydroxysuccinimide, to activate the surface carboxyl groups on the magnetic nanocrystal at room temperature for 40 minutes-18 hours or at 4° C. for 2 hours-24 hours, wherein the molar ratio between the magnetic nanocrystal and dicyclohexylcarbodiimide or the molar ratio between the magnetic nanocrystal and N,N-diisopropylcarbodiimide ranges from 1:2 to 1:2000, and the molar ratio between dicyclohexylcarbodiimide and N-hydroxysuccinimide or the molar ratio between N,N-diisopropylcarbodiimide and N-hydroxysuccinimide ranges from 1:0.9 to 1:10;

2) isolating the biocompatible magnetic nanocrystals with surface reactive N-hydroxysuccinimide ester moiety from the reaction solution obtained in step (1) and removing organic solvent, thereby obtaining a powder of the biocompatible magnetic nanocrystals bearing surface reactive N-hydroxysuccinimide ester moiety.

In the third aspect, the invention provides a method for preparing covalent conjugate of magnetic nanocrystal and biomolecule, comprising steps for mixing the powder of biocompatible magnetic nanocrystal bearing surface reactive N-hydroxysuccinimide ester moiety with a biomolecule bearing amino group in an aqueous medium, and incubating the reaction mixture at room temperature for 30 minutes-4 hours or at 4° C. for 2 hours-24 hours, thereby obtaining the covalent conjugate of the magnetic nanocrystal and the biomolecule, wherein the feed molar ratio between the magnetic nanocrystal bearing surface reactive N-hydroxysuccinimide ester moiety and the biomolecule ranges from 1:0.01 to 1:1000.

In the invention, the method for producing biocompatible magnetic nanocrystals is characterized by "one-pot" reaction. The direct products of the "one-pot" reaction, i.e., paramagnetic, superparamagnetic or ferromagnetic nanocrystals are biocompatible, highly soluble, and stably dispersible in physiological buffer. In addition, the nanocrystals possess high crystallinity degree, narrow particle size distribution, size tunability, and strong magnetic response to external magnetic fields. Most importantly, the surface reactive group is introduced to the resultant magnetic nanocrystal by using biocompatible macromolecule carrying two or more functional groups such as carboxyl group and/or amino group as surface capping reagent. In addition, the excellent dissolubility of the nanocrystal powder is greatly in favor of long-term storage and transport. Therefore, the magnetic nanocrystals either in liquid solution or in solid form exhibit great potentials in practical applications.

Furthermore, in the present invention, the powder of magnetic nanocrystals bearing surface reactive N-hydroxysuccinimide ester moiety is produced in an organic solvent by activating the surface carboxyl group on the magnetic nanocrystal using DCC/NHS or DIC/NHS as activator. The magnetic nanocrystals in powder form can thus covalently conjugate to the biomolecule bearing amino group after they are mixed in an aqueous solution. Moreover, after long-term storage in powder form, the magnetic nanocrystal bearing surface reactive N-hydroxysuccinimide ester moiety still retains reactivity with molecule bearing amino group. The powder of the magnetic nanocrystals bearing surface N-hydroxysuccinimide ester moiety can conveniently be stored, transported, and covalently conjugated to the biomolecule in a very simple way. The magnetic nanocrystal powder is therefore user-friendly and possesses great potentials in various types of biological and biomedical applications.

BRIEF DESCRIPTION OF THE DRAWINGS

FIG. 5A is the TEM image of the biocompatible magnetic $Fe_3O_4$ nanocrystals obtained before the introduction of additional reaction solution. The refluxing time was 2 h.

FIG. 5B is the particle size distribution of the biocompatible magnetic $Fe_3O_4$ nanocrystals shown in FIG. 5A.

FIG. 5C is the TEM image of the biocompatible magnetic $Fe_3O_4$ nanocrystals obtained by introducing additional reaction solution and prolonged refluxing process.

FIG. 5D is the particle size distribution of the biocompatible magnetic $Fe_3O_4$ nanocrystals shown in FIG. 5C.

Lane 1#: $Fe_3O_4$-(rch 24 mAb) conjugate;
Lane 2#: mixture of $Fe_3O_4$ nanocrystals and rch 24 mAb;
Lane 3#: pure $Fe_3O_4$ nanocrystals;
Lane 4#: pure rch 24 mAb.

Figure 10:
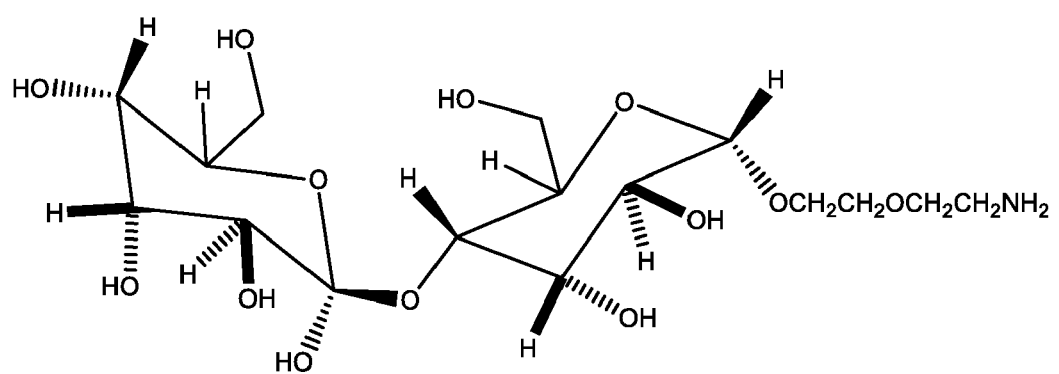

FIG. 10 is the molecular structure of the lactose used in Example 6.

Figure 11:
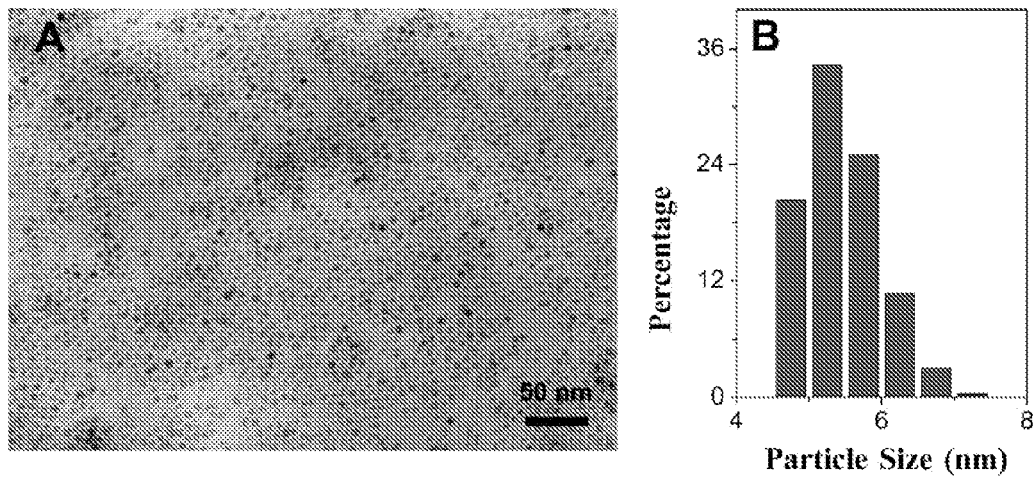

FIG. 11 is the TEM image (A) and the corresponding particle size distribution (B) of the nanocrystals provided by Example 9.

Figure 12:
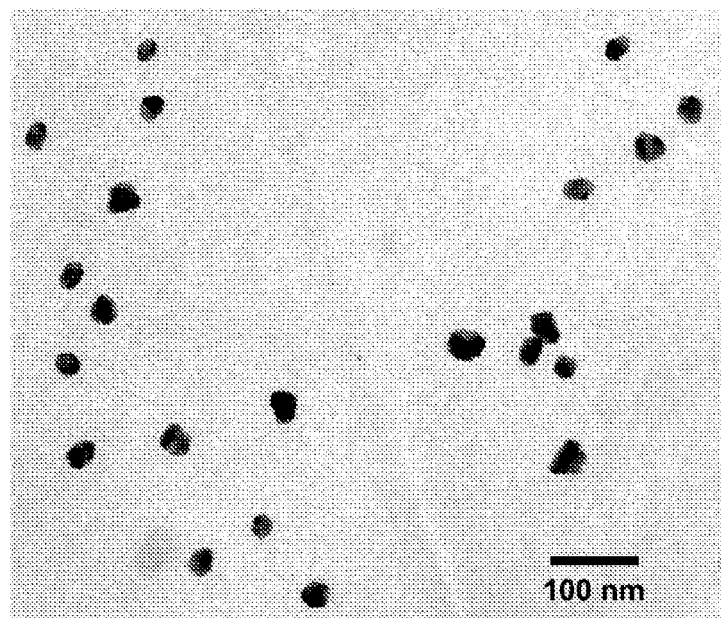

FIG. 12 is the TEM image of the Ni nanocrystals provided by Example 11.

Figure 13:
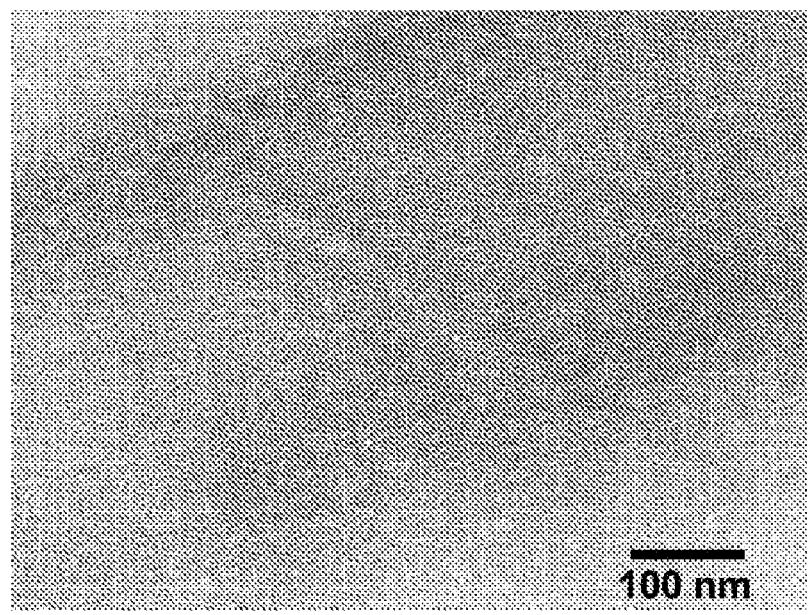

FIG. 13 is the TEM image of the $Er_2O_3$ nanocrystals provided by Example 19.

Figure 14:
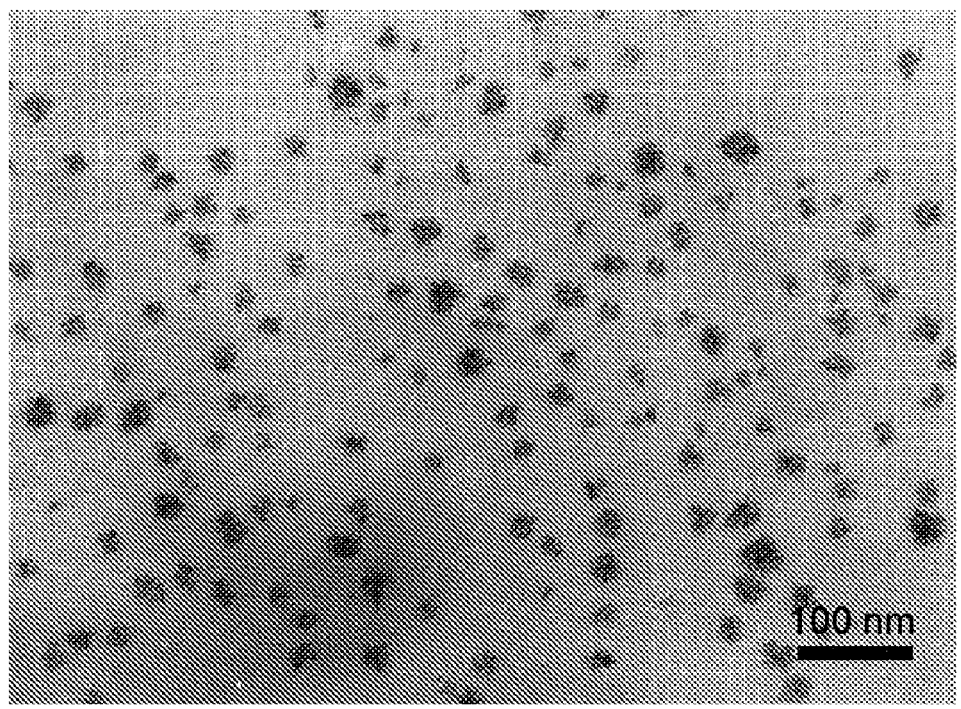

FIG. 14 is the TEM image of the $Fe_3O_4$ nanocrystals provided by Example 26.

Figure 15:
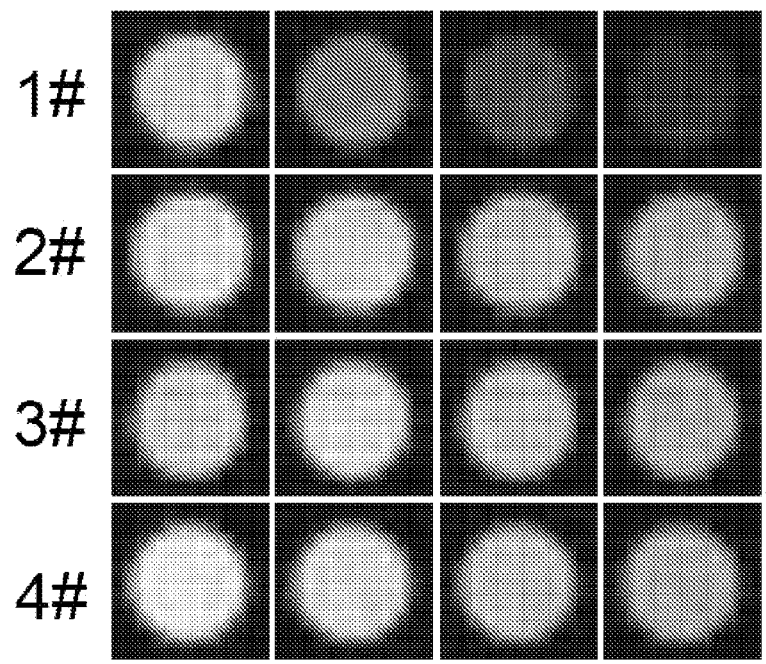

FIG. 15 is the $T_2$-weighted images of the cancer cell samples described in Example 30. From left to right, echo times are 25, 75, 125, 175 ms, respectively.

First row: Lysed cancer cell sample obtained after incubation with $Fe_3O_4$-(rch 24 mAb) conjugate.

Second row: Lysed cancer cell sample obtained after incubation with $Fe_3O_4$-IgG conjugate.

Third row: Lysed cancer cell sample obtained after incubation with $Fe_3O_4$ nanocrystals.

Fourth row: Lysed cancer cell sample obtained by following the same incubation procedures for the above samples except that neither proteins nor nanocrystals was presented during the incubation.

Figure 16:
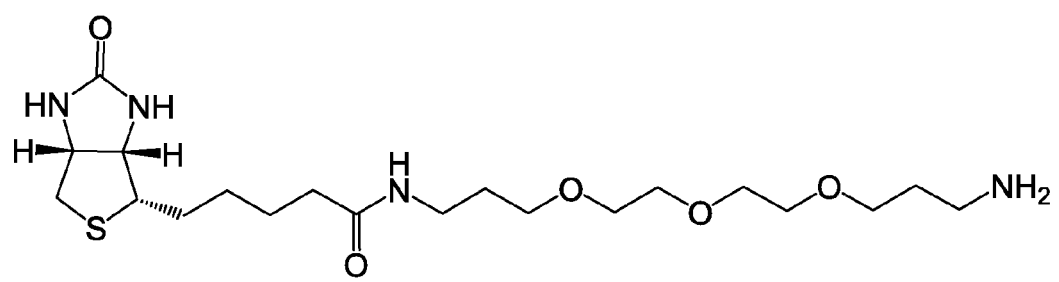

FIG. 16 is the molecular structure of the biotin-$PEO_3$-amine used in Example 32.

Figure 17:
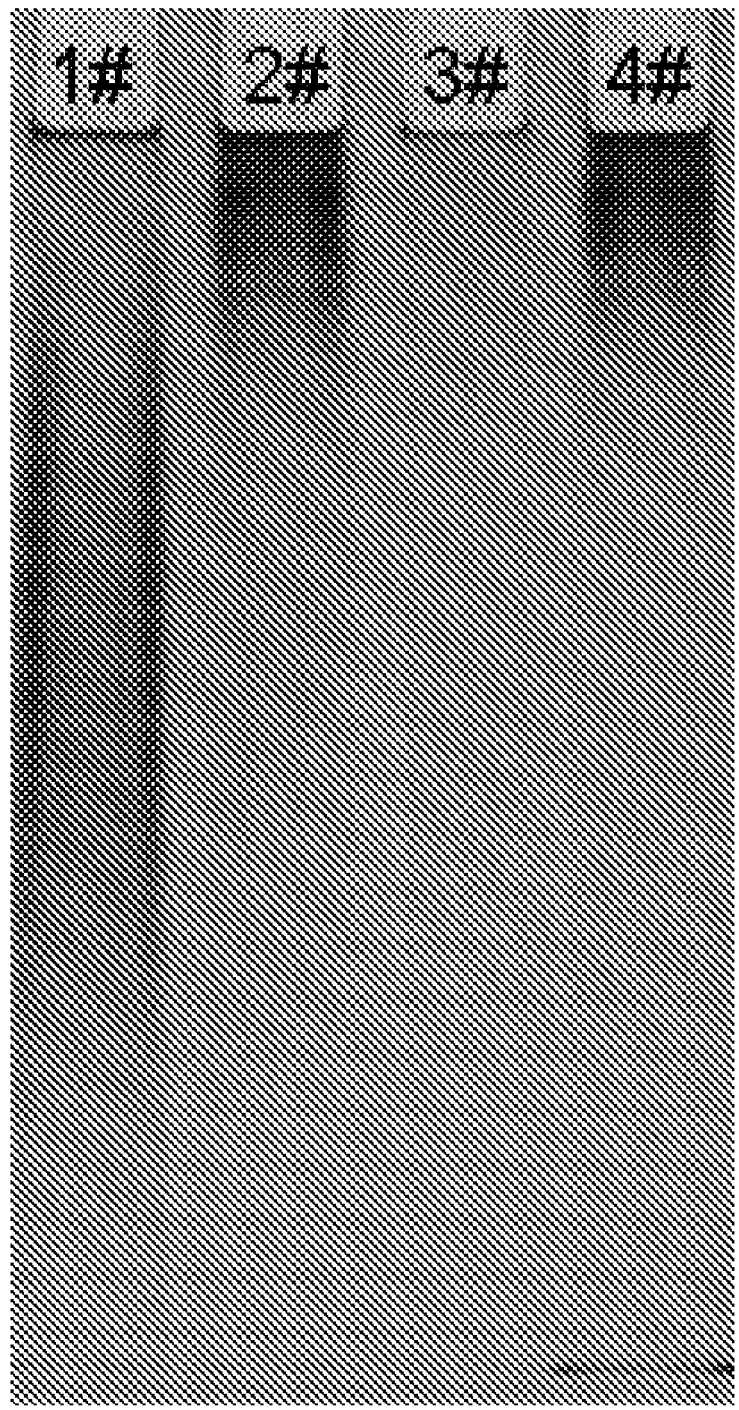

FIG. 17 is the electrophoresis result on $Fe_3O_4$-antibody conjugate in comparison with the corresponding controls as described in Example 34.

Lane 1#: $Fe_3O_4$-(rch 24 mAb) conjugate;
Lane 2#: mixture of $Fe_3O_4$ nanocrystals and rch 24 mAb;
Lane 3#: pure $Fe_3O_4$ nanocrystals;
Lane 4#: pure rch 24 mAb.

Reference Number

1. Magnet

DETAILED DESCRIPTION OF THE INVENTION

In the present invention, biocompatible magnetic nanocrystals with high crystallinity degree, high solubility, and excellent colloidal stability in physiological buffer are provided. The biocompatible magnetic nanocrystals are prepared by "one-pot" reaction through thermal decomposition of organometallic compound or metal-inorganic compound in non-polar or weak-polar solvent in the presence of different types of biocompatible macromolecules or in the presence of both biocompatible macromolecule and alkyl amine, alkyl carboxylic acid, or alkyl alcohol bearing different length of alkyl chain.

1. Biocompatible Magnetic Nanocrystal

In the invention, the biocompatible magnetic nanocrystals, which are highly soluble and stably dispersible in physiological buffer, are paramagnetic, superparamagnetic or ferromagnetic. The particle size ranges from 1 to 60 nm with a relative standard deviation of less than 15%. The surface of the magnetic nanocrystal is chemically modified by biocompatible macromolecule or simultaneously by biocompatible macromolecule and alkyl amine, alkyl carboxylic acid, or alkyl alcohol bearing different length of alkyl chain. The weight percentage of the biocompatible macromolecule in the magnetic nanocrystal sample ranges from 5% to 80%.

The alkyl amine, alkyl carboxylic acid, or alkyl alcohol bearing different length of alkyl chain participates in the formation of the nanocrystals and ultimately modified on the surface of the biocompatible nanocrystal via chemical bond. Preferably, the boiling points of the alkyl amine, alkyl carboxylic acid, or alkyl alcohol are above 160° C., for example, an alkyl amine having more than 7 $CH_2$ units, an alkyl carboxylic acid having more than 4 $CH_2$ units, and an alkyl alcohol or a polyol having more than 7 $CH_2$ units. The number of $CH_2$ units in the alkyl chain of amine, carboxylic acid, or alcohol chemically modified on the surface of the biocompatible nanocrystal ranges from 4 to 24, preferably from 10 to 18. The examples of particularly preferable amine, carboxylic acid, or alcohol in the present invention include oleylamine, oleic acid, n-decanoic acid, dodecyl amine, 1,2-hexadecanediol and the like.

The magnetic nanocrystal is mainly selected from magnetic transition metal and oxide thereof, magnetic lanthanide oxide, magnetic oxide doped with transition metal or lanthanide ion, preferably from Fe and oxide thereof, oxides of Gd, Tb, Dy, Ho, Er, and Tm, and Co, Ni, Mn and their oxides.

The molecular weight of the biocompatible macromolecules ranges from 600 to 20000, preferably from 600 to 6000, and the macromolecules are mainly chosen from linear or branched PEG bearing one or more carboxyl group(s) or amino group(s), and block copolymers consisting of a linear or branched PEG segment and a poly(acrylic acid), poly (methacrylic acid), poly(ethyleneimine), polyalanine, polylysine, polyleucine, poly(glutamic acid), poly(aspartic acid), polycaprolactone, poly(lactic acid), or poly(lactic-co-glycolic acid) segment. The biocompatible macromolecule bonded on the surface of the magnetic nanocrystal may offer one or more carboxyl groups or amino groups for further covalently conjugating the magnetic nanocrystal to biomolecule.

The solubility of the biocompatible magnetic nanocrystal powder remains in a range of 0.1 g/L to 60 g/L in physiological buffer after being stored for 6-month, and no precipitation occurs in the resultant colloidal solution in more than half year.

The physiological buffer is phosphate buffered saline (PBS), Dulbecco's phosphate-buffered saline (D-PBS), Hank's balanced salt solution (HBSS) or Earle's balanced salt solution (EBSS).

2. Method for Preparing the Biocompatible Magnetic Nanocrystal

The method for preparing biocompatible magnetic nanocrystal which is highly soluble and stably dispersible in physiological buffer via a one-pot reaction comprises following steps:

1) mixing an organometallic compound or a metal-inorganic compound (such as ferric acetylacetonate, etc.), biocompatible macromolecule (such as α,ω-dicarboxyl-terminated PEG2000, etc.), and amine (such as oleylamine, etc.), carboxylic acid (such as oleic acid, etc.), or alcohol (such as 1,2-hexadecanediol) in non-polar or weak-polar high boiling-point solvent (such as phenyl ether, etc.) to prepare a reaction mixture. The concentration of organometallic compound or metal-inorganic compound in pure solvent ranges from 0.001 to 0.2 mol/L, preferably from 0.01 to 0.1 mol/L; the concentration of the biocompatible macromolecule in pure solvent ranges from 0.001 mol/L to 1 mol/L, preferably from 0.05 mol/L to 0.6 mol/L; the concentration of alkyl amine, alkyl carboxylic acid or alkyl alcohol in pure solvent ranges from 0 to 0.2 mol/L, preferably from 0 to 0.1 mol/L; the number of $CH_2$ units in the alkyl molecule ranges from 4 to 20, preferably from 10 to 18, and the specific examples for the alkyl amine, alkyl carboxylic acid, and alkyl alcohol are oleylamine, oleic acid, n-decanoic acid, dodecyl amine, 1,2-hexadecanediol and the like;

2) purging the reaction system with nitrogen to remove oxygen, and then heating the resultant reaction mixture to decompose the metal precursor, thereby forming biocompatible magnetic nanocrystal. The reaction temperature ranges from 120 to 350° C., preferably from 180 to 280° C.; and the reaction time ranges from 0.5 to 50 hours, preferably from 1 to 25 hours.

3) cooling the reaction mixture obtained by step 2) to room temperature, introducing 5-40 fold volume of an organic solvent (such as ether, petroleum ether, methanol, ethanol, acetone or their mixtures, etc.) into the resultant solution to precipitate the magnetic nanocrystals and subsequently washing the precipitate for 3-5 times, collecting the biocompatible magnetic nanocrystals by centrifugation;

4) purifying the biocompatible magnetic nanocrystals dissolved in deionized water by dialysis against water for 12-48 hours;

5) precipitating the biocompatible nanocrystals from the aqueous solution obtained by step 4) and then washing the precipitate of the biocompatible magnetic nanocrystals for 3-5 times using an organic solvent (such as ether, petroleum ether, methanol, ethanol, acetone or their mixtures, etc.). After dried in vacuum or freeze-drying process, biocompatible magnetic nanocrystal powder, which can conveniently be stored and transported, is obtained;

6) dissolving the biocompatible magnetic nanocrystal powder obtained in step 5) physiological buffer to obtain a stable magnetic fluid.

In the invention, the particle size of the biocompatible magnetic nanocrystal is mainly controlled by the following parameters such as reaction temperature, reaction time, concentration of the metal precursor, the molecular weight and concentration of the biocompatible macromolecule. In addition, the size of the biocompatible magnetic nanocrystal prepared in the presence of different types of alkyl amines, alkyl carboxylic acids, or alkyl alcohols, in addition to the biocompatible macromolecule, is also controlled by the concentration and molecular weight of amine, carboxylic acid and alcohol as well.

The specific examples for the biocompatible macromolecule and the alkyl amine, alkyl carboxylic acid or alkyl alcohol are the same as those described in the "Biocompatible magnetic nanocrystal section".

The transition metal or rare-earth metal used in the current method may be selected from iron, cobalt, nickel, manganese and lanthanide. The metal-organic coordination compound used in the current method may be formed by a transition metal or rare-earth metal ion with an organic ligand selected from the group consisting of acetylacetonate, carbonyl, phenyl acetylacetonate, cyclopentadienyl, and N-nitrosophenylhydroxylamine. The precursor of magnetic nanocrystal used in the current method may be selected from the group consisting of oleate, stearate, acetate, gluconate, citrate, oxalate, chloride, sulfate, nitrate, and fatty acid salts of a transition metal or rare-earth metal ion, and hydrates of these salts. The non-polar high boiling-point solvent used in the current method is selected from phenyl ether, dibenzyl ether, dioctyl ether, 1-octadecene, oleylamine or derivatives thereof; the weak-polar high boiling-point solvent is selected from trioctylamine, tributylamine and the like. The boiling point of any of these solvents is above 160° C. Among them, boiling points of phenyl ether, dibenzyl ether, dioctyl ether, 1-octadecene and oleylamine are 259° C., 298° C., 291° C., 314° C. and 348-350° C., respectively; and boiling points of trioctylamine and tributylamine are 355-357° C. and 215° C., respectively. The nanocrystals mentioned in the present invention are prepared at the boiling point of any of these solvents or temperature higher than 160° C.

The organometallic compound is a metal-organic coordination compound formed by transition metal or lanthanide ion with organic ligand. It is chosen from ferric triacetylacetonate, ferrous acetylacetonate, iron pentacarbonyl, nickel acetylacetonate, nickel tetracarbonyl, cobalt acetylacetonate, cobalt(II) acetylacetonate, dicobalt octacarbonyl, manganese acetylacetonate, manganese(II) acetylacetonate, cyclopentadienyl manganese tricarbonyl, gadolinium acetylacetonate, phenyl gadolinium acetylacetonate, tris(cyclopentadienyl) gadolinium, terbium acetylacetonate, tris(cyclopentadienyl) terbium, dysprosium acetylacetonate, tris(cyclopentadienyl) dysprosium, holmium acetylacetonate, tris(cyclopentadienyl) holmium, erbium acetylacetonate, tris(cyclopentadienyl) erbium, thulium acetylacetonate, tris(cyclopentadienyl) thulium, organometallic compounds formed by N-nitrosophenylhydroxylamine ($C_6H_5N(NO)O^-$) ligand with iron, cobalt, nickel, manganese, gadolinium, terbium, dysprosium, holmium or erbium ion, and so on.

The metal compound useful for preparing the biocompatible magnetic nanocrystal of the present invention, other than the above-mentioned organometallic compound, is chosen from organic or inorganic salts and organic or inorganic salt hydrates of transition metals or lanthanide metals. The specific examples include metal oleate, stearate, acetate, gluconate, citrate, oxalate, chloride, sulfate, nitrate, and metal fatty acid salt, and hydrates thereof, such as ferric acetate, ferric oxalate, iron oleate, iron stearate, nickel oxalate, nickel citrate, nickel acetate, nickel oleate, nickel stearate, cobalt acetate, cobalt oxalate, cobalt citrate, cobalt decanoate, cobalt oleate, cobalt stearate, manganese acetate, manganese oxalate, manganese citrate, manganese gluconate, cobalt oleate, cobalt stearate, gadolinium acetate, gadolinium oxalate, gadolinium oleate, gadolinium stearate, terbium acetate, terbium oxalate, terbium oleate, terbium stearate, dysprosium acetate, dysprosium oxalate, dysprosium oleate, dysprosium stearate, holmium acetate, holmium oxalate, holmium oleate, holmium stearate, erbium acetate, erbium oxalate, erbium oleate, erbium stearate, thulium acetate, or thulium oxalate, thulium oleate, thulium stearate, ferric chloride, ferrous chloride, ferric chloride tetrahydrate, ferric chloride hexahydrate, ferrous sulfate, nickel chloride, nickel chloride hexahydrate, cobalt chloride, cobalt chloride hexahydrate, manganese chloride, gadolinium chloride, gadolinium chloride trihydrate, gadolinium chloride hexahydrate, gadolinium nitrate, gadolinium sulfate, gadolinium sulfate octahydrate, terbium chloride, terbium chloride hexahydrate, terbium nitrate, terbium sulfate, terbium sulfate octahydrate, dysprosium chloride, dysprosium chloride hexahydrate, dysprosium nitrate, dysprosium sulfate, dysprosium sulfate octahydrate, holmium chloride, holmium chloride hexahydrate, holmium nitrate, holmium sulfate, holmium sulfate octahydrate, erbium chloride, erbium chloride hexahydrate, erbium nitrate, erbium sulfate, or erbium sulfate octahydrate, thulium chloride, thulium chloride hexahydrate, thulium nitrate, thulium sulfate, or thulium sulfate octahydrate, and so on.

3. Powder of Biocompatible Magnetic Nanocrystal Bearing Surface Reactive N-Hydroxysuccinimide Ester Moiety In the invention, biocompatible magnetic nanocrystal bearing surface reactive group derived from the macromolecule chemically modified on the nanocrystal surface is prepared by using the same biocompatible macromolecule as mentioned above except that the biocompatible macromolecule bears at least two functional groups selected from carboxyl groups and amino groups. Consequently, the biocompatible macromolecule bonded to the nanocrystal surface offers one or more carboxyl groups or amino groups for further covalently coupling the magnetic nanocrystal with biomolecule.

In the case that the surface reactive group presents on the surface of the magnetic nanocrystal is carboxyl group, the carboxyl group can further be activated to form N-hydroxysuccinimide ester moiety by activators, so as to produce a biocompatible magnetic nanocrystal bearing surface reactive N-hydroxysuccinimide ester moiety. The activator used for converting the carboxyl group to N-hydroxysuccinimide ester moiety may be N-hydroxysuccinimide/dicyclohexylcarbodiimide (NHS/DCC) or N-hydroxysuccinimide/N,N-diisopropylcarbodiimide (NHS/DIC). The activation reaction is performed in organic solvent, so as to produce the powder of biocompatible magnetic nanocrystal with surface reactive N-hydroxysuccinimide ester moiety.

The resultant powder of magnetic nanocrystals with surface reactive N-hydroxysuccinimide ester moiety can be used to further covalently conjugate the magnetic nanocrystal to a biomolecule bearing amino group by directly mixing the magnetic nanocrystal with the biomolecule in an aqueous solution. In the resultant bioconjugate, the molar ratio between the magnetic nanocrystal and the biomolecule ranges from 1:0.01 to 1:1000. The biomolecule bearing amino group is chosen from amino acids, peptides, proteins, or derivatives of carbohydrates and nucleic acids bearing amino group, and etc.

The powder of the magnetic nanocrystals bearing surface reactive N-hydroxysuccinimide ester moiety, after being stored at 4° C. in dark for one year, still retains reactivity with the biomolecule bearing amino group.

4. Method for Preparing a Powder of Biocompatible Magnetic Nanocrystal Bearing Surface Reactive N-Hydroxysuccinimide Ester Moiety The method for preparing the powder of biocompatible magnetic nanocrystal bearing surface reactive N-hydroxysuccinimide ester moiety comprises following steps:

1) introducing an organic solution of NHS followed by an organic solution of DCC or DIC into an organic solution of the biocompatible magnetic nanocrystals with surface carboxyl group to activate the carboxyl group at room temperature (15-30° C.) for 40 minutes-18 hours or at 4° C. for 2-24 hours. The molar ratio between the magnetic nanocrystal and DCC or the molar ratio between the magnetic nanocrystal and DIC ranges from 1:2 to 1:2000, respectively, and the molar ratio between DCC and NHS or between DIC and NHS ranges from 1:0.9 to 1:10, respectively; or introducing an organic solution of DCC or DIC dropwise into an organic solution containing both magnetic nanocrystals bearing surface carboxyl group and NHS to activate the carboxyl group at room temperature (15-30° C.) for 40 minutes-18 hours or at 4° C. for 2 hours-24 hours. The molar ratio between the magnetic nanocrystal and DCC or the molar ration between the magnetic nanocrystal and DIC ranges from 1:2 to 1:2000, and the molar ratio between DCC and NHS or the molar ratio between DIC and NHS ranges from 1:0.9 to 1:10;

2) isolating and purifying the biocompatible magnetic nanocrystals bearing surface N-hydroxysuccinimide ester moiety from the reaction solution obtained in step 1) by removing the reaction byproducts via centrifugation, thereby obtaining an organic solution of the biocompatible magnetic nanocrystals with surface N-hydroxysuccinimide ester moiety.

3) drying the organic solution of the biocompatible magnetic nanocrystals obtained in step 2) in vacuum, thereby obtaining the powder of the biocompatible magnetic nanocrystals bearing surface N-hydroxysuccinimide ester moiety.

The organic solvent used in the activation reaction is chosen from dichloromethane, trichloromethane, tetrahydrofuran, ethyl acetate, ethylene glycol dimethyl ether, 1,4-dioxane, pyridine, N,N-dimethylformamide, dimethyl sulfoxide or the mixtures of any two above.

5. A Covalent Conjugate of Magnetic Nanocrystal and Biomolecule

The covalent conjugation between the magnetic nanocrystals bearing surface reactive N-hydroxysuccinimide ester moiety in powder form and biomolecule bearing amino group comprises the following steps: the powder of magnetic nanocrystals is mixed with biomolecule bearing amino group in an aqueous solution. After the reaction mixture was incubated for 30 minutes-4 hours at room temperature (15-30° C.) or 2 hours-24 hours at 4° C., their covalent conjugate is obtained. The molar ratio between the magnetic nanocrystal and the biomolecule in the resultant conjugate ranges from 1:0.01 to 1:1000.

The biomolecule bearing amino group, as mentioned above, is chosen from amino acids, peptides, proteins, or derivatives of carbohydrates and nucleic acids bearing amino group.

EXAMPLES

Example 1

Figure 1:
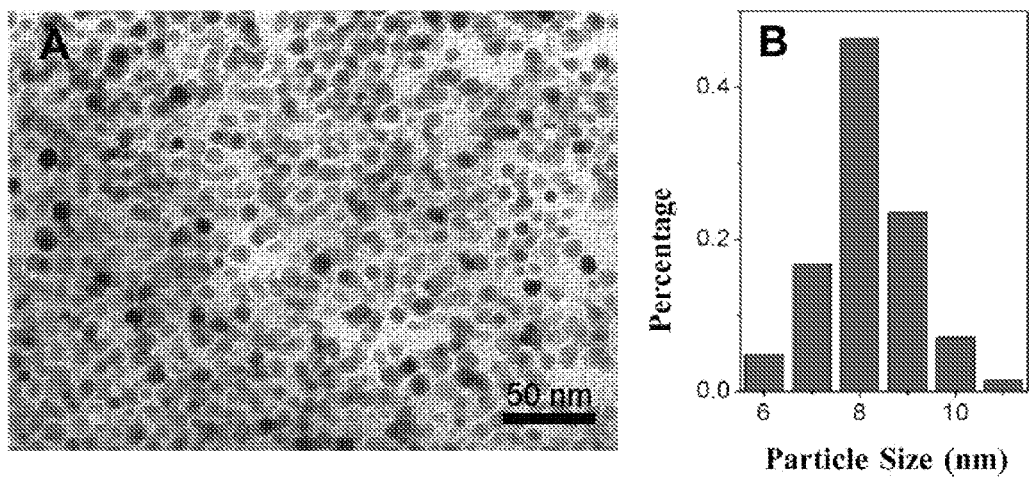
FIG. 1 is the transmission electron microscope (TEM) image (A) of the nanocrystals provided by Example 1 and the corresponding particle size distribution (B).
Figure 2:
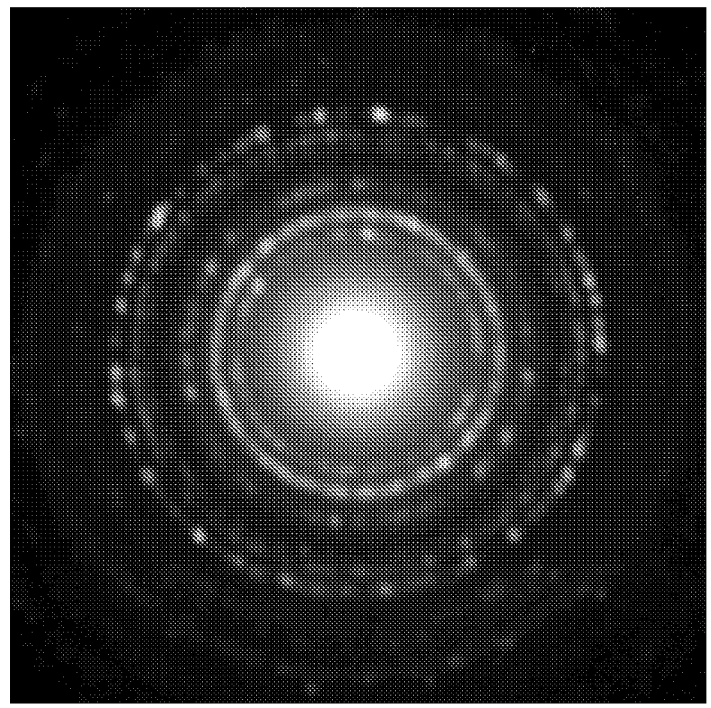
FIG. 2 is the electron diffraction pattern of the nanocrystals provided by Example 1.
Figure 3:
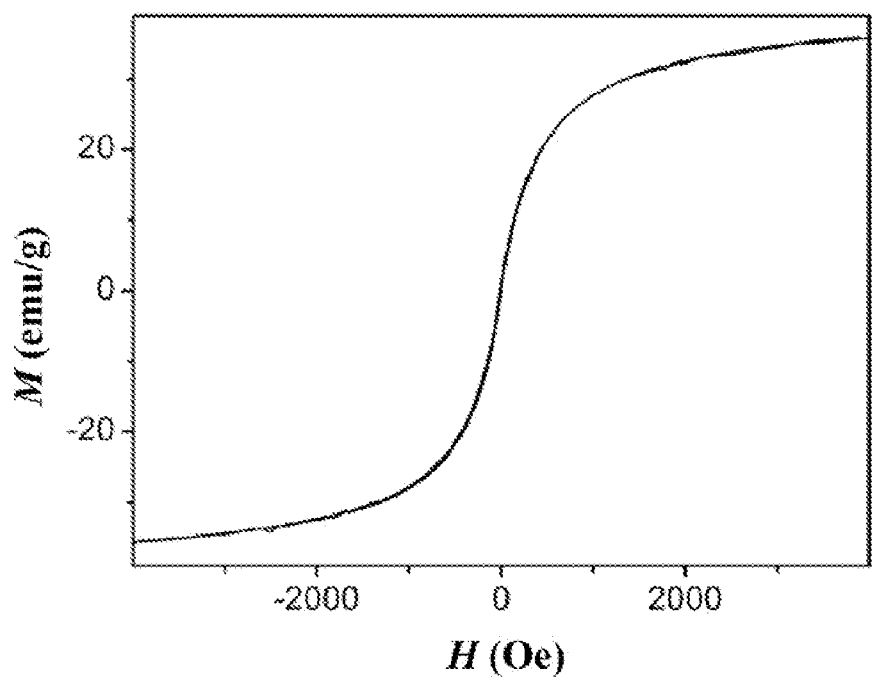
FIG. 3 is the room-temperature magnetization curve of the nanocrystals provided by Example 1.

1.06 g Fe(acac)$_3$, 12 g α,ω-dicarboxyl-terminated PEG2000 (prepared according to reference, see: *Adv. Mater.*, (2005) 17(8), 1001) and 3.87 mL oleylamine were dissolved in 50 mL phenyl ether, then the solution was transferred to a 100 mL three-necked flask. After being purged with nitrogen for 30 minutes, the solution was refluxed for 20 hours. The reaction was terminated by cooling the reaction system to room temperature. The resultant magnetic nanocrystals bearing surface carboxyl group were precipitated and washed three times by ether. The biocompatible magnetic nanocrystals were collected by centrifugation. Subsequently, the Fe$_3$O$_4$ nanocrystals were redissolved in deionized water. After dialysis against pure water for 24 hours, the Fe$_3$O$_4$ nanocrystals were precipitated again and then washed by a mixture of ether and acetone (V:V=3:1). Via vacuum drying, a black powder of the biocompatible magnetic nanocrystals which can be stored and transported conveniently was obtained. The powder sample was characterized by transmission electron microscopy (TEM). FIG. 1 shows a representative TEM image of the magnetic nanocrystals together with the corresponding particle size distribution. The biocompatible magnetic Fe$_3$O$_4$ nanocrystals are spherical with a narrow size distribution. The mean particle size is of 8.2 nm with a relative standard deviation of 10%. The electron diffraction pattern of this sample, shown in FIG. 2, demonstrates that the biocompatible magnetic nanocrystals are highly crystallized magnetite. Thermal gravity analysis demonstrates that the total organic content in the biocompatible nanocrystal sample is around 60%. The room-temperature magnetization curve, shown in FIG. 3, demonstrates the magnetic nanocrystals are superparamagnetic with a saturation magnetization of 35.7 emu/g. The solubility of the biocompatible magnetic nanocrystals in PBS is determined to be above 60 g/L at 25° C.

Example 2

Figure 4:
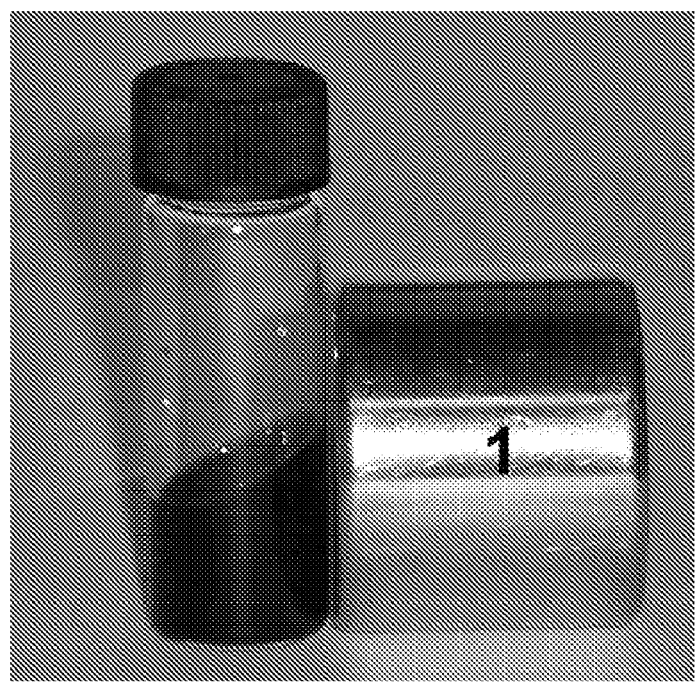
FIG. 4 is the photograph of the magnetic fluid prepared by Example 2. The photograph was captured by placing the solution near a permanent magnet.

The dissolvability of the biocompatible magnetic nanocrystals in powder form obtained by Example 1 was tested after the nanocrystals being kept at room temperature for half a year by completely dissolving 0.6 g powder sample in 100 mL 0.01 M PBS (pH=7.4) buffer. FIG. 4 shows a photograph of the resultant buffer solution of the powder sample. The photograph was captured by placing the magnetic fluid near a permanent magnet. No precipitates were presented in the resultant magnetic fluid after it was stored for half year.

Example 3

Figure 5:
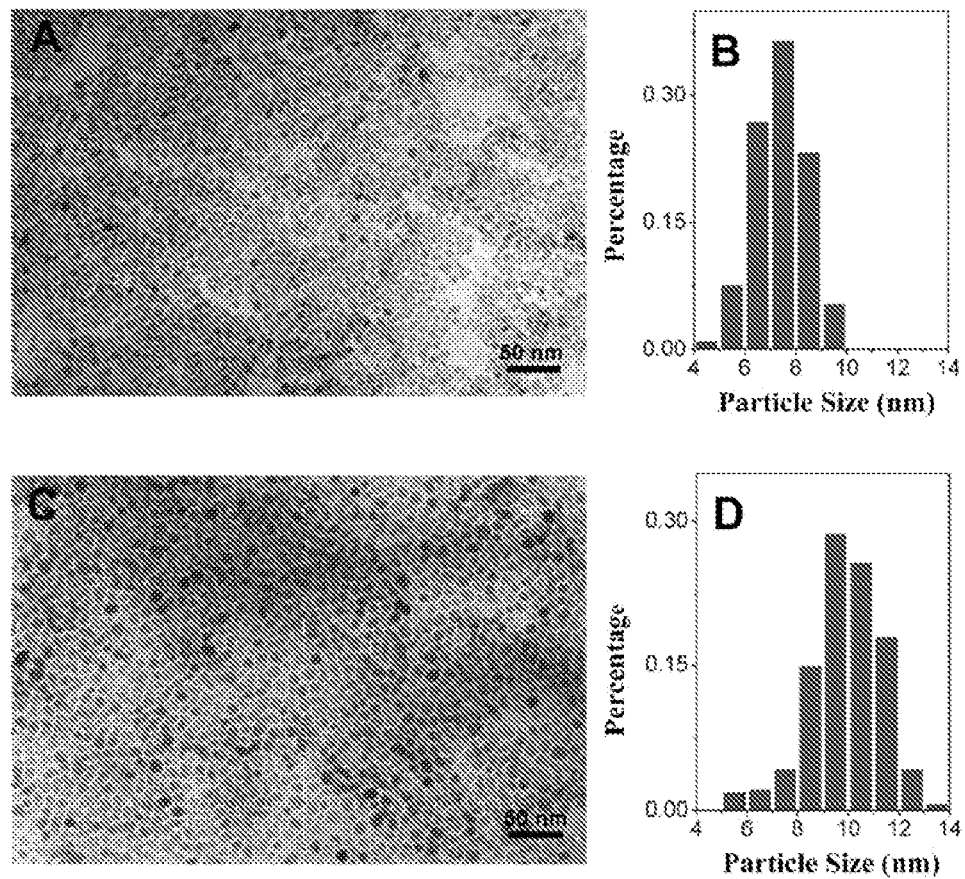
FIG. 5 shows the effects of refluxing time on the biocompatible magnetic $Fe_3O_4$ nanocrystals prepared by Example 3.

4.24 g $Fe(acac)_3$, 48 g $\alpha,\omega$-dicarboxyl-terminated PEG2000 and 15.5 mL oleylamine were dissolved in 200 mL phenyl ether, then the solution was transferred to a 250 mL three-necked flask. After being purged with nitrogen for 50 min, 140 mL reaction solution was extracted and then transferred into a pressure equalizing funnel mounted on the three-necked flask. The reaction solution remained in the flask was then refluxed for 2 hours. After that, 140 mL stock solution in the pressure equalizing funnel was introduced dropwise into the flask under reflux conditions. After the whole dripping process lasted for 2 hours was completed, the refluxing process was kept going for another 20 hours for growing larger nanocrystals in comparison with those shown in Example 1. The following processing procedures for purification, isolation and vacuum drying were the same as those described in Example 1. FIG. 5 presents TEM images and the particle size distributions of the magnetic $Fe_3O_4$ nanocrystals obtained right before the introduction of 140 mL stock solution (A, B) and after the whole reaction process was completed (C, D), respectively. The TEM results demonstrate that due to the secondary introduction of additional reaction solution and prolonged refluxing process, the mean particle size of the biocompatible magnetic nanocrystals is effectively increased from 7.4 nm to 9.9 nm.

Example 4

Figure 6:
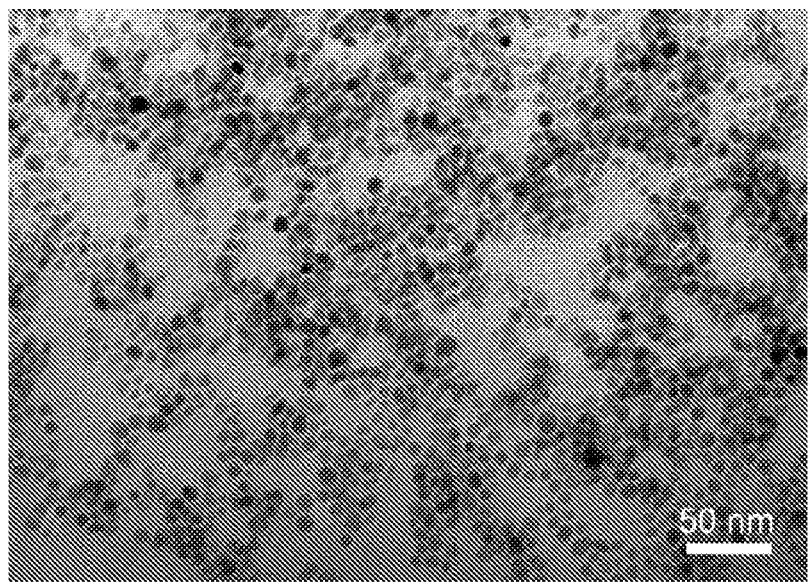
FIG. 6 is TEM image of $Fe_3O_4$ nanocrystals provided by Example 4 before the surface carboxyl group was activated.
Figure 7:
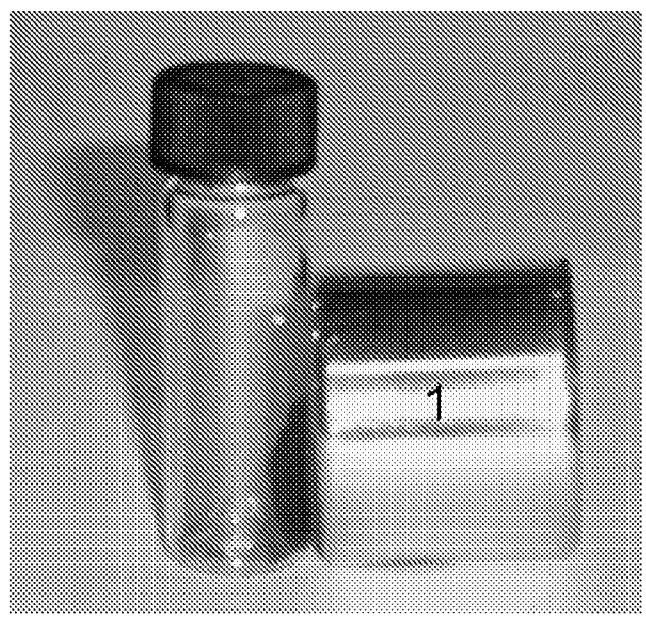
FIG. 7 is the powder sample of the $Fe_3O_4$ nanocrystals provided by Example 4 after the nanocrystal surface carboxyl group was converted to N-hydroxysuccinimide ester moiety. The photograph was captured by placing the powder sample near a permanent magnet.

The surface reactive carboxyl group on the biocompatible magnetic nanocrystals, prepared by a similar method given in Example 1 except for the difference in size of the resultant nanocrystals, was converted to N-hydroxysuccinimide ester moiety in the presence of NHS and DCC. In detail, 0.32 g magnetic $Fe_3O_4$ nanocrystals (10 nm) were dissolved in 50 mL N,N-dimethylformamide containing 17.3 mg (0.15 mmol) NHS (Aldrich 130672, >98%). Into this mixture, 1 mL N,N-dimethylformamide solution containing 30.9 mg (0.15 mmol) DCC (Fluka 36650, >99%) was then introduced dropwise. After the reaction took place at room temperature (25° C.) for 12 hours, the reaction mixture was subjected to centrifugation to remove the precipitates. Subsequently, the resultant supernatant was dried in vacuum to obtain a powder sample of the magnetic nanocrystals whose surface carboxyl group had been activated to N-hydroxysuccinimide ester moiety. FIG. 6 is a TEM image of the magnetic $Fe_3O_4$ nanocrystals captured before activation reaction. FIG. 7 is a photograph of the magnetic $Fe_3O_4$ nanocrystals in powder form obtained after the activation reaction. The photograph was captured by placing the particle sample near a permanent magnet.

Example 5

Figure 8:
FIG. 8 is the aqueous solution of the biocompatible magnetic nanocrystals mentioned in Example 5. It was prepared by dissolving a dry powder of the biocompatible magnetic nanocrystals bearing surface reactive N-hydroxysuccinimide ester moiety in PBS buffer. The photograph was captured by placing the solution near a permanent magnet.
Figure 9:
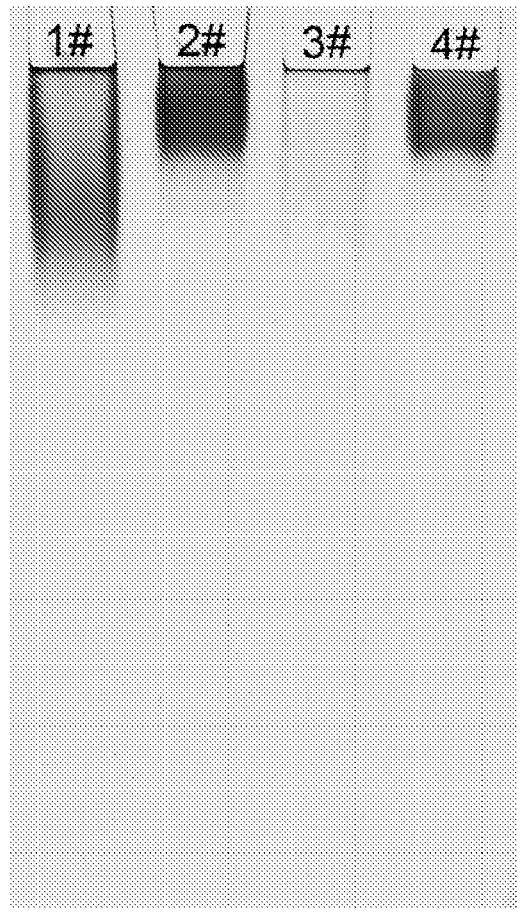
FIG. 9 is the electrophoresis result on $Fe_3O_4$-antibody conjugate in comparison with the corresponding controls as described in Example 5.

The powder sample of the biocompatible magnetic nanocrystals bearing surface N-hydroxysuccinimide ester moiety can simply be used to covalently conjugate to proteins such as antibody in physiological buffer. 10 mg magnetic nanocrystals, as obtained in Example 4, were mixed with 10 mL PBS buffer solution (pH=7.4) containing 1 mg/mL anti-carcino-embryonic antigen (CEA) monoclonal antibody rch 24 (rch 24 mAb). After incubating the reaction mixture at 20° C. for 4 hours, covalent conjugate of the magnetic $Fe_3O_4$ nanocrystals and the antibody was obtained. FIG. 8 shows a photograph of $Fe_3O_4$ nanocrystals in the aqueous solution prepared by dissolving a powder of magnetic $Fe_3O_4$ nanocrystals bearing surface N-hydroxysuccinimide ester moiety in PBS buffer. 5% (w/v) native polyacrylamide gel electrophoresis was adopted to evaluate the conjugation reaction. FIG. 9 shows a photograph of the 5% polyacrylamide separating gel stained after the electrophoresis experiment. Lanes 1, 2, 3 and 4 were filled with $Fe_3O_4$-(rch 24 mAb) conjugate, mixture of $Fe_3O_4$ and rch 24 mAb, $Fe_3O_4$, and rch 24 mAb, respectively. There is nearly no difference between lanes 2 and 4, while there is a huge difference between lanes 1 and 4, demonstrating that rch 24 mAb antibody has conjugated to the negatively charged $Fe_3O_4$ nanocrystals. The difference between lanes 1 and 2 demonstrates the conjugation reaction between $Fe_3O_4$ and rch 24 mAb is based on covalent bonding rather than nonspecific interactions.

Example 6

The activation reaction for converting the surface reactive carboxyl group on the biocompatible magnetic nanocrystals to N-hydroxysuccinimide ester moiety can also be carried out in different types of organic solvents. For example, 0.23 g magnetic $Fe_3O_4$ nanocrystals (8.2 nm) provided by Example 1 were dissolved in 100 mL chloroform containing 57.7 mg (0.5 mmol) NHS. Into this mixture, 1 mL chloroform solution containing 41.2 mg (0.2 mmol) DCC was then introduced dropwise. After the reaction took place at 25° C. for 12 hours, the reaction mixture was subjected to centrifugation to remove the precipitates. After drying the resultant supernatant in vacuum, a powder sample of the magnetic nanocrystals bearing surface N-hydroxysuccinimide ester moiety was obtained. 10 mg powder sample of the activated nanocrystals and 1 mg lactose (molecular structure is given in FIG. 10) were dissolved in 20 mL deionized water. After incubating the reaction system for 40 minutes at 25° C., the conjugate of magnetic $Fe_3O_4$ nanocrystal and lactose was obtained. The appearances of C=O vibrational band at 1690 $cm^{-1}$ and C—N band at 1260 $cm^{-1}$ in the infrared spectrum of the final product confirmed the formation of covalent conjugate.

Example 7

2.32 g magnetic $Fe_3O_4$ nanocrystals (10 nm), prepared by a similar method in Example 1 except for the difference in the size of the nanocrystals, and 18.4 mg (0.16 mmol) NHS were dissolved in 50 mL N,N-dimethylformamide, then 1 mL dichloromethane solution containing 30.9 mg (0.15 mmol) DCC was introduced dropwise into above solution. The reaction was allowed for 40 minutes at 30° C., then reaction mixture was subjected to centrifugation to remove precipitates. After being washed for 3 times using N,N-dimethylformamide, the precipitates were discarded. The N,N-dimethylformamide solutions used for cleaning the precipitates were then combined with the supernatant. After drying in vacuum, a powder of the magnetic nanocrystals bearing surface N-hydroxysuccinimide ester moiety was finally obtained. 10 mg of the above powder was dissolved in 10 mL PBS buffer containing 4 mg human insulin. After incubating the reaction mixture at 25° C. for 2 hours, covalent conjugate of the magnetic nanocrystals and insulin was obtained. Electrophoresis experiments similar to those described in Example 5 demonstrated a successful conjugation of the magnetite nanocrystals to insulin.

Example 8

10 mg magnetic nanocrystals bearing surface N-hydroxysuccinimide ester moiety, obtained according to Example 4, were firstly dissolved in 5 mL PBS buffer. Subsequently, the resultant solution was mixed with 10 mL PBS buffer solution (pH=7.4) containing 10 mg L-Lysine. The reaction was allowed for 4 hours under gentle shaking at 20° C., then the conjugate of magnetic nanocrystals and L-Lysine was obtained. The resultant conjugate in aqueous solution was purified by dialysis against pure water for 7 hours to remove un-reacted L-Lysine. The amount of the un-reacted L-Lysine was measured by ultra-violet-visible spectroscopy through a color reaction (ninhydrin reaction) which generated purple color. The experiment results demonstrated that the number of L-Lysine molecules on each nanocrystal was about 300.

Example 9

0.53 g Fe(acac)$_3$, 6 g monocarboxyl-terminated PEG2000 (prepared according to reference, see: *Adv. Mater.*, (2005) 17(8), 1001) and 1.93 mL oleylamine were dissolved in 25 mL phenyl ether, then the solution was transferred to a 50 mL three-necked flask. After being purged with nitrogen for 30 minutes, the solution was refluxed for 12 hours. The reaction was terminated by cooling the reaction system to room temperature. The resultant magnetic nanocrystals were precipitated, washed three times by ether and then collected by centrifugation. The Fe$_3$O$_4$ nanocrystals obtained were dissolved in deionized water for further purification by dialyzing the aqueous solution of the nanocrystals against pure water for 24 hours. Then, a powder of the Fe$_3$O$_4$ nanocrystals was obtained by similar procedures described in Example 1. The nanocrystal powder can conveniently be stored and transported. Furthermore, the nanocrystal powder was demonstrated to be well dissolved in physiological buffer after long-term storage with a solubility up to 50 g/L. The nanocrystals were characterized with transmission electron microscopy (TEM). FIG. 11 shows a representative TEM image of the magnetic nanocrystals (FIG. 11A) together with the corresponding particle size distribution (FIG. 11B). The average particle size of the biocompatible magnetic Fe$_3$O$_4$ nanocrystals is of 5.3 nm.

Example 10

0.176 g Fe(acac)$_3$, 2 g α,ω-dicarboxyl-terminated PEG4000 and 0.157 mL oleic acid were dissolved in 25 mL dibenzyl ether, then the solution was transferred to a 50 mL three-necked flask. After being purged with nitrogen for 30 minutes, the solution was refluxed for 1 hour. The reaction was terminated by cooling the reaction system to room temperature. The resultant magnetic nanocrystals were precipitated, washed three times by ether and then collected by centrifugation. The Fe$_3$O$_4$ nanocrystals obtained were subsequently dissolved in deionized water for a further purification by dialysis. A powder sample of the Fe$_3$O$_4$ nanocrystals was obtained by drying the resultant aqueous solution. The average particle size of the resultant nanocrystals bearing surface carboxyl group is of 5.4 nm. The solubility of the nanocrystals was determined to be 58 g/L.

Example 11

0.073 g Ni(acac)$_2$, 0.5 g monocarboxyl-terminated PEG2000 and 0.115 mL oleylamine were dissolved in 20 mL phenyl ether, then the solution was transferred to a 50 mL three-necked flask. After being purged with nitrogen for 60 minutes, the solution was refluxed for 3 hours. The reaction was terminated by cooling the reaction system to room temperature. The resultant magnetic nanocrystals were precipitated, washed three times by ether and then collected by centrifugation. The following processing procedures were similar to those described Example 1. The resultant Ni nanocrystals have particle size of 30-60 nm. The content of the biocompatible macromolecules was estimated to be 5% by weight. FIG. 12 shows a TEM image of the resultant nanocrystals.

Example 12

1.22 g C$_5$H$_5$Mn(CO)$_3$ (cyclopentadienyl manganese tricarbonyl), 24 g α,ω-dicarboxyl-terminated PEG6000 and 2.56 mL oleic acid were dissolved in 200 mL phenyl ether, then the solution was transferred to a 250 mL three-necked flask. After being purged with nitrogen for 60 minutes, the solution was refluxed for 25 hours. The reaction was terminated by cooling the reaction system to room temperature. The following processing procedures were similar to those described in Example 1. The particle size of the resultant biocompatible Mn$_3$O$_4$ oxide nanocrystals bearing surface carboxyl group is in a range of 15 to 30 nm. The existence of the surface carboxyl group was demonstrated by a literature method, see: *Journal of Colloid and Interface Science*, (2007) 311, 469.

Example 13

0.588 g Fe(CO)$_5$ and 12 g PEG2000 terminated by one carboxyl group and one amino group were dissolved in 50 mL phenyl ether, then the solution was transferred to a 100 mL three-necked flask. After being purged with nitrogen for 40 minutes, the reaction solution was heated to 200° C. and maintained at this temperature for 10 hours. The reaction was terminated by cooling the reaction system to room temperature. The following processing procedures were similar to those described in Example 1. The resultant biocompatible nanocrystals bearing surface amino group are ferromagnetic with a particle size in a range of 10-17 nm. Infrared spectroscopy was used to demonstrate the existence of amino residues on the particle surface. The PEG2000 terminated by one carboxyl group and one amino group was synthesized by coupling one of carboxyl group from α,ω-dicarboxyl-terminated PEG2000 with one of the amino group from 1,2-ethylenediamine via amidation reaction.

Example 14

1.29 g Ni(acac)$_2$, 20 g block copolymer of PEG-b-poly (lactic acid) (synthesized chemical, the synthesis started from polymerization of lactic acid initiated by a PEG2000-based initiator followed by a further reaction with maleic anhydride. The molecular weight was in a range of 3000-5000) were dissolved in 50 mL oleylamine, then the solution was transferred to a 100 mL three-necked flask. After being purged with nitrogen for 30 minutes, the reaction solution was heated to 280° C. and maintained at this temperature for 8 hours. The reaction was terminated by cooling the reaction system to room temperature. The resultant biocompatible magnetic nanocrystals were precipitated, washed three times by a mixture of ether and acetone (V:V=5:1) and then collected by centrifugation. The following processing procedures were similar to those described in Example 1. The particle size of the biocompatible magnetic nanocrystals finally obtained is in a range of 10 to 15 nm. The mass percent of the biocompatible macromolecules in the nanocrystal sample is around 40%.

Example 15

1.06 g Fe(acac)$_3$, 12 g block copolymer of PEG-b-poly(acrylic acid) (synthesized chemical, the synthesis started from polymerization of acrylic acid initiated by PEG2000-based macromolecular initiator via ATRP approach, the molecular weight was about 5500, see reference: *Langmuir* (2005) 21(9), 4205), and 3.5 g dodecylamine were dissolved in 50 mL phenyl ether, then the solution was transferred to a 100 mL three-necked flask. After being purged with nitrogen for 30 minutes, the reaction solution was refluxed for 10 hours. The reaction was terminated by cooling the reaction system to room temperature. The following processing procedures were similar to those described in Example 1. The particle size of the biocompatible magnetic Fe$_3$O$_4$ nanocrystals finally obtained was in a range of 5 to 13 nm.

Example 16

1.0 g iron stearate, 12 g branched PEG20000 with carboxyl group, and 0.5 g n-decanoic acid were added into 50 mL 1-octadecene, then the solution was transferred to a 100 mL three-necked flask. After being purged with nitrogen for 40 minutes, the solution was refluxed for 1 hour. The reaction was terminated by cooling the reaction system to room temperature. The following purifying procedures were similar to those described in Example 1. The size of the resultant biocompatible magnetic Fe$_3$O$_4$ nanocrystals bearing surface carboxyl group is of 6 to 10 nm. The content of the macromolecule in the resultant nanocrystal sample was estimated to be 80% by weight.

Example 17

2.94 g gadolinium acetylacetonate, 12.0 g α,ω-dicarboxyl-terminated PEG2000 and 11.9 mL oleylamine were dissolved in 200 mL phenyl ether, then the solution was transferred to a 250 mL three-necked flask. After being purged with nitrogen for 60 minutes, the solution was heated to 100° C. to remove trace water under vacuum. Then the reaction solution was refluxed for 3 hours. The reaction was terminated by cooling the reaction system to room temperature. The following purifying and drying processes were similar to those described in Example 1. The average particle size of the biocompatible paramagnetic Gd$_2$O$_3$ nanocrystals obtained is of 3.9 nm.

Example 18

0.35 g paramagnetic gadolinium oxide nanocrystals, obtained in Example 17, and 11.5 mg (0.1 mmol) NHS were dissolved in 50 mL chloroform, then 1 mL chloroform containing 8.24 mg (0.04 mmol) DCC was introduced dropwise into above solution. After being kept at 25° C. for 12 hours, the reaction solution was subjected to centrifugation to remove precipitates. By drying the resultant supernatant in vacuum, a powder sample of gadolinium oxide nanocrystals bearing surface N-hydroxysuccinimide ester moiety was obtained. 10 mg powder of the activated nanocrystals was then dissolved in 5 mL PBS buffer solution containing 10 mg human IgG. After incubating the reaction mixture at 4° C. for 24 hours, covalent conjugate of gadolinium oxide nanocrystals and IgG was obtained. Electrophoresis experiments similar to those described in Example 5 demonstrated a successful conjugation of the gadolinium oxide particles to IgG.

Example 19

0.452 g erbium acetylacetonate, 1.82 g α,ω-dicarboxyl-terminated PEG2000 and 1.8 mL oleylamine were dissolved in 30 mL phenyl ether, then the solution was transferred to a 50 mL three-necked flask. After being purged with nitrogen for 60 minutes, the solution was heated to 85° C. to remove trace water under vacuum. Then the reaction solution was refluxed for 5 hours. The reaction was terminated by cooling the reaction system to room temperature. The following processing procedures were similar to those described in Example 1. The biocompatible erbium oxide magnetic nanocrystals bearing surface carboxyl group are paramagnetic with an average particle size of 3.2 nm. FIG. 13 is the TEM image of the magnetic nanocrystals.

Example 20

0.81 g paramagnetic erbium oxide nanocrystals, obtained in Example 19, and 67.9 mg NHS (0.59 mmol) were dissolved in 30 mL dichloromethane, then 2 mL dichloromethane containing 49.5 mg DCC (0.24 mmol) was introduced dropwise into above solution. After being kept at 25° C. for 8 hours, the reaction solution was subjected to centrifugation to remove precipitates. By drying the resultant supernatant in vacuum, a powder sample of erbium oxide nanocrystals bearing surface N-hydroxysuccinimide ester moiety was obtained. 10 mg of the above powder was then dissolved in 5 mL PBS buffer solution (pH=7.4) containing 4 mg anti-gastric cancer monoclonal antibody 3H11. After incubating the reaction mixture at 4° C. for 6 hours, covalent conjugate of erbium oxide nanocrystals and 3H11 was obtained. Electrophoresis experiments similar to those described in Example 5 demonstrated a successful conjugation of erbium oxide nanocrystals to 3H11.

Example 21

0.444 g dysprosium acetylacetonate, 1.81 g α,ω-dicarboxyl-terminated PEG2000, and 0.916 g n-decanoic acid were dissolved in 30 mL phenyl ether, then the solution was transferred to a 50 mL three-necked flask. After being purged with nitrogen for 60 minutes, the reaction solution was refluxed for 5 hours. The reaction was terminated by cooling the reaction system to room temperature. The following purifying and drying processes were similar to those described in Example 1. The biocompatible dysprosium oxide nanocrystals bearing surface carboxyl group were obtained. The particle size is of 1-3 nm.

Example 22

0.351 g holmium chloride hexahydrate, 0.917 g α,ω-dicarboxyl-terminated PEG2000, and 1.8 mL oleylamine were dissolved in 30 mL phenyl ether, then the solution was transferred to a 50 mL three-necked flask. After being purged with nitrogen for 60 minutes, the reaction solution was refluxed for 5 hours. The reaction was terminated by cooling the reaction system to room temperature. The following purifying and drying processes were similar to those described in Example 1. The biocompatible paramagnetic holmium oxide nanocrystals bearing surface carboxyl group were obtained. The average particle size was of 7.5 nm.

Example 23

2.96 g cobalt stearate, 12 g monocarboxyl-terminated PEG6000 and 0.5 g n-decanoic acid were added in 30 mL 1-octadecene, then the solution was transferred to a 50 mL three-necked flask. After being purged with nitrogen for 45 minutes, the reaction solution was refluxed for 1 hour. The reaction was terminated by cooling the reaction system to room temperature. The following purifying and drying processes were similar to those described in Example 1. The biocompatible $Co_3O_4$ magnetic nanocrystals of 10-20 nm were obtained.

Example 24

1.5 g iron stearate, 6 g α,ω-dicarboxyl-terminated PEG2000, and 0.5 g 1,2-hexadecanediol were added into 30 mL dibenzyl ether, then the solution was transferred to a 50 mL three-necked flask. After being purged with nitrogen for 45 minutes, the reaction solution was refluxed for 1 hour. The reaction was terminated by cooling the reaction system to room temperature. The following purifying and drying processes were similar to those described in Example 1. The biocompatible $Fe_3O_4$ magnetic nanocrystals bearing surface carboxyl group obtained are of 5-12 nm.

Example 25

0.531 g ferric acetylacetonate, 0.096 g manganese(II) acetylacetonate, 6 g α,ω-dicarboxyl-terminated PEG4000, and 1.94 g 1,2-hexadecanediol were dissolved into 25 mL dibenzyl ether, then the solution was transferred to a 50 mL three-necked flask. After being purged with nitrogen for 30 minutes, the reaction solution was refluxed for 12 hours. The reaction was terminated by cooling the reaction system to room temperature. The resultant Mn-doped $Fe_3O_4$ nanocrystals bearing surface carboxyl group were precipitated and washed three times by ether. The biocompatible magnetic nanocrystals were collected by centrifugation and then dissolved in deionized water for further purification by dialysis. The following processing procedures were similar to those described in Example 1. A powder sample of the biocompatible Mn-doped $Fe_3O_4$ nanocrystals bearing surface carboxyl group was finally obtained. The average particle size is of 6.8 nm.

Example 26

1.06 g Fe(acac)$_3$, 12 g α,ω-dicarboxyl-terminated PEG600 and 3.87 mL oleylamine were dissolved in 50 mL phenyl ether, then the solution was transferred to a 100 mL three-necked flask. After being purged with nitrogen for 30 minutes, the solution was refluxed for 8 hours. The reaction was terminated by cooling the reaction system to room temperature. The resultant magnetic nanocrystals were precipitated and washed three times by a mixture of petroleum ether and ether (V:V=3:1). Then, the nanocrystals collected by centrifugation were re-dissolved in deionized water for further purification by dialyzing the resultant aqueous solution against pure water for 36 hours. FIG. 14 presents a TEM image of the biocompatible magnetic $Fe_3O_4$ nanocrystals finally obtained. The particle size is in a range of 13 to 33 nm.

Example 27

1.18 g magnetic cobalt nanocrystals (20 nm) and 67.9 mg (0.59 mmol) NHS were dissolved in 30 mL tetrahydrofuran, then 2 mL tetrahydrofuran containing 134 mg (0.65 mmol) DCC was added dropwise into the above solution. The following reaction was allowed for 24 hours at 4° C., then reaction mixture was subjected to centrifugation to remove precipitates. After being washed for 3 times using tetrahydrofuran, the precipitates were discarded. The tetrahydrofuran solutions used for cleaning the precipitates were then combined with the supernatant. Via vacuum drying, a powder sample of the magnetic nanocrystals whose surface carboxyl group had been activated to N-hydroxysuccinimide ester moiety was finally obtained. 10 mg of the above powder was mixed with 1.64 mg L-Lysine in 2 mL PBS buffer (pH=7.4). The conjugation reaction was allowed at 4° C. for 2 hours, covalent conjugate of cobalt nanocrystals and L-lysine was then obtained. The amount of the un-reacted L-Lysine was measured by ultra-violet-visible spectroscopy through a color reaction (ninhydrin reaction) which generated purple color. The experiment results demonstrated that the number of L-Lysine molecules on each cobalt nanocrystal was about 800.

Example 28

3.75 g magnetic nickel nanocrystals (30 nm), obtained by a similar method described in Example 11 except for the difference in particle size, were dissolved in 80 mL dichloromethane. Then, 1 mL N,N-dimethylformamide containing 138 mg (1.2 mmol) NHS and 1 mL dichloromethane containing 37.8 mg (0.3 mmol) DIC (Fluka 38370, >98%) were successively introduced into the above solution. After being kept at 15° C. for 18 hours, the reaction solution was subjected to centrifugation to remove precipitates. By drying the resultant supernatant in vacuum, a powder sample of Ni nanocrystals bearing surface N-hydroxysuccinimide ester moiety was obtained. 10 mg of the above powder sample was dissolved in 5 mL TE (Tri(hydroxymethyl)aminomethane-ethylenediaminetetraacetic acid disodium salt) solution containing 4.67 mg 5'-Amine-$C_6$TA CAG GTC ATG TAA CTT-3c. After incubating the reaction mixture at 28° C. for 30 minutes, covalent conjugate of Ni nanocrystals and DNA was obtained. A shift of 8 nm with respect to the surface plasmon resonance peak of the Ni nanocrystals was observed after the conjugation reaction, demonstrating that the DNA molecules were successfully conjugated to Ni nanocrystals.

Example 29

2.29 g magnetic $Mn_3O_4$ nanocrystals (2 nm), prepared by a similar method in Example 12, and 11.5 mg (0.1 mmol) NHS were dissolved in 50 mL 1,4-dioxane, then 1 mL 1,4-dioxane containing 30.9 mg (0.15 mmol) DCC was introduced dropwise into above solution. After being kept at 4° C. for 2 hours, the reaction solution was subjected to centrifugation to remove precipitates. By drying the resultant supernatant in vacuum, a powder sample of $Mn_3O_4$ nanocrystals bearing surface N-hydroxysuccinimide ester moiety was obtained. 10 mg of the powder was then dissolved in 5 mL PBS buffer solution containing 10 mg human IgG. After incubating the reaction mixture at 4° C. for 24 hours, covalent conjugate of Mn$_3$O$_4$ nanocrystals and IgG was obtained. Electrophoresis experiments similar to those described in Example 5 demonstrated a successful conjugation of Mn$_3$O$_4$ nanocrystals to IgG.

Example 30

50 μL PBS buffer solution of the Fe$_3$O$_4$-(rch 24 mAb) conjugate obtained in Example 5 was incubated with 2×10$^6$ human colon carcinoma cells (LS 180) with CEA being expressed on the cell surface in 1 mL PBS at 37° C. for 1 h. Then, the cells were collected by centrifugation followed by a washing procedures using PBS for 3 times. 200 μL 0.1% sodium dodecyl sulfate (SDS) was used to lyse the cells in PBS buffer. In parallel, two additional cell samples were prepared by incubating the carcinoma cells with Fe$_3$O$_4$-IgG conjugate and Fe$_3$O$_4$, respectively, following the above procedures. In addition, another cell sample was prepared according to the above procedures except that the incubation process was carried out in the absence of neither magnetic nanocrystals nor foreign proteins (rch 24 mAb or IgG). The aforementioned four lysed cell samples were measured by magnetic resonance imaging technique. T$_2$-weighted images shown in FIG. 15 clearly demonstrate that only the cell sample obtained after being incubated with Fe$_3$O$_4$-(rch 24 mAb) conjugate present a much shorter proton T$_2$ relaxation time. In contrast, no obvious difference is presented among the rest cell samples. This result demonstrates that the Fe$_3$O$_4$-(rch 24 mAb) conjugate can specifically target tumor cells (LS 180 cells) via the antibody-antigen interactions.

Example 31

0.58 g Dy$_2$O$_3$ nanocrystals (2.3 nm) bearing surface carboxyl group, obtained in Example 21, and 138 mg (1.2 mmol) NHS were dissolved in 30 mL dichloromethane, then 2 mL dichloromethane containing 37.8 mg (0.3 mmol) DIC was introduced dropwise into above solution. After being kept at 25° C. for 6 hours, the reaction solution was subjected to centrifugation to remove precipitates. By drying the resultant supernatant in vacuum, a powder sample of Dy$_2$O$_3$ nanocrystals bearing surface N-hydroxysuccinimide ester moiety was obtained. The presence of N-hydroxysuccinimide ester moiety in the resultant nanocrystal sample was confirmed by infrared spectroscopy.

Example 32

10 mg Fe$_3$O$_4$ nanocrystals bearing surface N-hydroxysuccinimide ester moiety, obtained according to Example 4, and 0.5 mg of a water-soluble biotin derivative, i.e., Biotin-PEO$_3$-amine (molecular structure is shown in FIG. 16), were dissolved in 20 mL deionized water. The following reaction was allowed for 1 hour at 25° C., the conjugate of magnetic nanocrystals and biotin was obtained. The successful conjugation was confirmed by infrared spectroscopy. For example, the infrared spectrum of the conjugate presents vibrational bands at 1680 cm$^{-1}$ and 3340 cm$^{-1}$ for C=O and N—H from amido group, respectively.

Example 33

0.8 g Mn-doped Fe$_3$O$_4$ nanocrystals bearing surface carboxyl group, obtained in Example 25, and 138 mg (1.2 mmol) NHS were dissolved in 30 mL chloroform, then 2 mL chloroform containing 37.8 mg (0.3 mmol) DIC was introduced dropwise. The activation reaction was allowed for 6 hours at 25° C. The reaction mixture was subjected to centrifugation to remove precipitates. A powder sample of the Mn-doped Fe$_3$O$_4$ nanocrystals bearing surface N-hydroxysuccinimide ester moiety was obtained by drying the supernatant in vacuum. Further conjugation reaction was performed to conjugate the doped nanocrystals to antibody rch 24. A successful conjugation was demonstrated by electrophoresis experiments similar to those described in Example 5.

Example 34

A PBS buffer solution (0.01 M, pH=6.5) of Fe$_3$O$_4$ nanocrystals bearing surface carboxyl group was prepared by redissolving the powder sample obtained in Example 1 at a concentration of 5 g/L. Into 0.5 mL freshly prepared solution of the nanocrystals, 2 μmol 1-ethyl-3-(3-dimethylaminopropyl) carbodiimide hydrochloride (EDC.HCl) and 5 μmol hydroxysulfosuccinimide sodium salt (Sulfo-NHS) were introduced. The activation reaction was allowed for 15 minutes at room temperature and then 0.5 mL PBS solution containing 1 mg anti-carcinoembryonic antigen (CEA) monoclonal antibody rch 24 (rch 24 mAb) was introduced. The conjugation reaction was carried out at room temperature for 4 hours. In parallel, three additional control experiments were performed under exactly the same conditions except that neither EDC.HCl nor Sulfo-NHS was present in the reaction systems. 5% (w/v) native polyacrylamide gel electrophoresis was adopted to evaluate the conjugation reaction. FIG. 17 shows a photograph of the separating gel stained after the electrophoresis experiment. Lanes 1, 2, 3 and 4 were filled with Fe$_3$O$_4$-(rch 24 mAb) conjugate, mixture of Fe$_3$O$_4$ and rch 24 mAb, Fe$_3$O$_4$, and rch 24 mAb, respectively.

Example 35

0.212 g Fe(acac)$_3$ and 2.4 g α,ω-dicarboxyl-terminated PEG2000 were dissolved in 15 mL phenyl ether, then the solution was transferred to a 25 mL three-necked flask. After being purged with nitrogen for 30 minutes, the solution was refluxed for 18 hours. The reaction was terminated by cooling the reaction system to room temperature. The following purifying and drying processes were similar to those described in Example 1. The average particle size of the biocompatible Fe$_3$O$_4$ magnetic nanocrystals bearing surface carboxyl group was of 7.7 nm with a standard deviation of 8.7%. As mentioned above, the current nanocrystal sample was prepared in a rather similar way to those described in Examples 1, 2 and 10 except that none of alkyl amine, alkyl carboxylic acid or alkyl alcohol was presented in the reaction system. Consequently, the solubility of the current nanocrystal sample was only of 1 g/L in PBS buffer.

Example 36

0.531 g Fe(acac)$_3$ and 6 g α,ω-dicarboxyl-terminated PEG4000 were dissolved in 25 mL trioctylamine, then the solution was transferred to a 50 mL three-necked flask. After being purged with nitrogen for 30 minutes, the solution was refluxed for 8 hours. The reaction was terminated by cooling the reaction system to room temperature. The resultant magnetic nanocrystals were precipitated, washed three times by ether, and then collected by centrifugation. After the supernatant was decanted, the precipitate was dried and then redissolved in deionized water for further purification by dialysis. The follow processing procedures were similar to those described in Example 1 for obtaining a powder of biocompatible nanocrystals. The size of the resultant nanocrystals was 5-9 nm. Nanocrystals of 3-8 nm were obtained when tributylamine was used instead of trioctylamine.

Example 37

A reaction mixture was prepared using the recipe given in Example 10 except that oleic acid was replaced by equal molar hexadecanoic acid or arachidic acid. By the same preparation procedures described in Example 10, magnetic nanocrystals of 3-15 nm were obtained.

Example 38

7.2 g ferric stearate, 80 g monocarboxyl-terminated PEG2000, 2.28 g oleic acid, 20 mL phenyl ether and 20 mL 1-octadecene were mixed in a 250 mL three-necked flask. After being purged with nitrogen for 30 minutes, the solution was refluxed for 0.5 hour. The reaction was terminated by cooling the reaction system to room temperature. The resultant magnetic nanocrystals were precipitated, washed three times by ether, and then collected by centrifugation. After the supernatant was decanted, the precipitate was dried and then redissolved in deionized water for further purification by dialysis against pure water. The dialysis was lasted for 48 hours. The follow processing procedures were similar to those described in Example 1 for obtaining a powder of biocompatible nanocrystals. The size of the resultant nanocrystals was of 4-9 nm.

Example 39

0.6 g Fe(acac)$_3$ and 6 g block copolymer (molecular weight~8000) formed by monocarboxyl-terminated PEG4000 and branched poly(ethyleneimine) were dissolved in 25 mL tributylamine. The reaction mixture was transferred into a 50 mL three-necked flask. After being purged with nitrogen for 30 minutes, the solution was refluxed for 8 hours. The reaction was terminated by cooling the reaction system to room temperature. The resultant magnetic nanocrystals were precipitated, washed three times by a mixture of ether and petroleum ether, and then collected by centrifugation. After the supernatant was decanted, the precipitate was dried and then redissolved in deionized water for further purification by dialysis against pure water. The dialysis was lasted for 24 hours. The follow processing procedures were similar to those described in Example 1 for obtaining a powder of biocompatible nanocrystals bearing surface amino group. The size of the resultant nanocrystals was of 3-15 nm.

Example 40

0.6 g Fe(acac)$_3$ and 6 g block copolymer (molecular weight~10000) consisting of a PEG4000 segment and a poly (lactic acid) segment were dissolved in 25 mL phenyl ether. The reaction mixture was transferred into a 50 mL three-necked flask. After being purged with nitrogen for 30 minutes, the reaction mixture was heated to 220° C. and maintained at this temperature for 4 hours. The reaction was terminated by cooling the reaction system to room temperature. The resultant magnetic nanocrystals were precipitated, washed three times by a mixture of methanol and ether, and then collected by centrifugation. After the supernatant was decanted, the precipitate was dried and then redissolved in deionized water for further purification by dialysis against pure water. The dialysis was lasted for 24 hours. The follow processing procedures were similar to those described in Example 1 for obtaining a powder of biocompatible nanocrystals. The size of the resultant nanocrystals was of 9-22 nm.

Example 41

0.70 g Fe(cup)$_3$ (cup=$C_6H_5N(NO)O^-$) and 6 g α,ω-dicarboxyl-terminated PEG4000 were dissolved in 25 mL dioctyl ether. The reaction mixture was transferred into a 50 mL three-necked flask. After being purged with nitrogen for 30 minutes, the reaction mixture was refluxed for 4 hours. The reaction was terminated by cooling the reaction system to room temperature. The resultant magnetic nanocrystals were precipitated, washed three times by ether, and then collected by centrifugation. After the supernatant was decanted, the precipitate was dried and then redissolved in deionized water for further purification by dialysis against pure water. The dialysis was lasted for 20 hours. The follow processing procedures were similar to those described in Example 1 for obtaining a powder of biocompatible nanocrystals. The size of the resultant nanocrystals was of 7-11 nm.

Example 42

0.85 g Gd(cup)$_3$ (prepared according to literature, *Analytical Chemistry*, (1954) 26:883) and 6 g α,ω-dicarboxyl-terminated PEG4000 were dissolved in 25 mL trioctylamine. The reaction mixture was transferred into a 50 mL three-necked flask. After being purged with nitrogen for 30 minutes, the reaction mixture was refluxed for 4 hours. The reaction was terminated by cooling the reaction system to room temperature. The resultant magnetic nanocrystals were precipitated, washed three times by ether, and then collected by centrifugation. After the supernatant was decanted, the precipitate was dried and then redissolved in deionized water for further purification by dialysis against pure water. The dialysis was lasted for 24 hours. The follow processing procedures were similar to those described in Example 1 for obtaining a powder of biocompatible paramagnetic $Gd_2O_3$ nanocrystals. The size of the resultant nanocrystals was of 3-8 nm.

Example 43

0.6 g Fe(acac)$_3$ and 6 g block copolymer (molecular weight~6000) consisting of a PEG2000 segment and a polyalanine segment were dissolved in 25 mL phenyl ether. The reaction mixture was transferred into a 50 mL three-necked flask. After being purged with nitrogen for 30 minutes, the reaction mixture was heated to 200° C. and maintained at this temperature for 2 hours. The reaction was terminated by cooling the reaction system to room temperature. The resultant magnetic nanocrystals were precipitated, washed three times by a mixture of methanol and ether, and then collected by centrifugation. After the supernatant was decanted, the precipitate was dried and then redissolved in deionized water for further purification by dialysis against pure water. The dialysis was lasted for 24 hours. The follow processing procedures were similar to those described in Example 1 for obtaining a powder of biocompatible magnetic nanocrystals. The size of the resultant nanocrystals was of 8-15 nm.

Further preparations demonstrated that similar block copolymers containing a segment of PEG and a segment of polyamino acid such as polylysine, polyleucine, poly (glutamic acid), poly(aspartic acid) can be used to replace PEG-b-polyalanine for preparing various types of biocompatible nanocrystals according to Examples 11, 12, 14, 17, 19, 21, 23, 40 and 43.

Example 44

0.212 g Fe(acac)₃ and 2.6 g block copolymer (molecular weight~8000) consisting of a PEG2000 segment and a polycaprolactone segment (prepared according to literature, *Acta Polymerica Sinica* (2006) 5:740) were dissolved in 15 mL phenyl ether. The reaction mixture was transferred into a 25 mL three-necked flask. After being purged with nitrogen for 40 minutes, the reaction mixture was refluxed for 2 hours. The reaction was terminated by cooling the reaction system to room temperature. The following isolating, purifying and drying procedures were similar to those described Example 1. The size of the resultant nanocrystals was of 10-16 nm.

REFERENCES

1. Rockenberger, J. et al., A New Nonhydrolytic Single-Precursor Approach to Surfactant-Capped Nanocrystals of Transition Metal Oxides, *J. Am. Chem. Soc.* 121:11595-11596 (Nov. 24, 1999).
2. Nikhil R. Jana et al., Size- and Shape-Controlled Magnetic (Cr, Mn, Fe, Co, Ni) Oxide Nanocrystals via a Simple and General Approach, *Chem. Mater.* 16:3931-3935 (Nov. 9, 2004).
3. Jongnam Park et al., Ultra-large-scale syntheses of monodisperse nanocrystals, *Nature materials*, 3:891-895 (2004).
4. Taeghwan Hyeon et al., Synthesis of Highly Crystalline and Monodisperse Maghemite Nanocrystallites without a Size-Selection Process, *J. Am. Chem. Soc.*, 123:12798-12801 (Nov. 29, 2001).
5. Shouheng Sun et al., Size-Controlled Synthesis of Magnetite Nanoparticles, *J. Am. Chem. Soc.*, 124:8204-8205 (Apr. 11, 2002).
6. Zhen Li et al., Size-Controlled Synthesis of Magnetite Nanoparticles, *Chem. Mater.*, 16:1391-1393 (Apr. 20, 2004).
7. Zhen Li et al., Size-Controlled Synthesis of Magnetite Nanoparticles, *Chem. Mater.*, 16:1391-1393 (Apr. 20, 2004).
8. Zhen Li et al., Preparation of Water Soluble Magnetite Nanocrystals from Hydrated Ferric Salts in 2-Pyrrolidone Mechanism Leading to Fe₃O₄, *Angew. Chem. Int. Ed.*, 44:123-126 (2005).
9. Zhen Li et al., One-Pot Reaction to Synthesize Biocompatible Magnetite Nanoparticles, *Adv. Mater.*, 17:1001-1005 (Apr. 18, 2005).
10. Fengqin Hu et al., Preparation of Biocompatible Magnetite Nanocrystals for In Vivo Magnetic Resonance Detection of Cancer, *Adv. Mater.*, 18:2553-2555 (2006).
11. Greg T. Hermanson, Bioconjugate Techniques, *Academic Press, New York*, p. 173-176 (1996).
12. Fengqin Hu et al., Preparation of Biocompatible Magnetite Nanocrystals for In Vivo Magnetic Resonance Detection of Cancer, *Adv. Mater.*, 18:2553-2555 (2006).
13. Zhen Li et al., One-Pot Reaction to Synthesize Biocompatible Magnetite Nanoparticles, *Adv. Mater.*, 17:1001-1005 (Apr. 18, 2005).
14. Zhen Li et al., One-Pot Reaction to Synthesize Biocompatible Magnetite Nanoparticles, *Adv. Mater.*, 17:1001-1005 (Apr. 18, 2005).
15. Fengqin Hu et al., Preparation of magnetite nanocrystals with surface reactive moieties by one-pot reaction, *J. Colloid Interface Sci.*, 311:469-474 (2007).
16. Haijun Niu et al., Amphiphilic ABC Triblock Copolymer-Assisted Synthesis of Core-Shell Structured CdTe Nanowires, *Langmuir*, 21:4205-4210 (2005).
17. Alexander I. Popov et al., Cupferron and Neocupferron Complexes of Rare Earth Elements, *Anal. Chem.*, 26:883-886 (1954).
18. Guoqiang Yu et al. Synthesis of poly(ε-caprolactone)/poly(ethylene glycol) block copolymers and surface property control of their microspheres, *Acta Polymerica Sinica*, 5:740-744 (2006)

The invention claimed is:

1. A biocompatible magnetic nanocrystal highly soluble and dispersible in a physiological buffer characterized in that the surface of said biocompatible magnetic nanocrystal is bonded with a biocompatible macromolecule and an alkyl-containing molecule simultaneously, wherein said alkyl-containing molecule is selected from the group consisting of an alkyl amine, an alkyl carboxylic acid, and an alkyl alcohol, and wherein the number of $CH_2$ units in the alkyl-containing molecule ranges from 4 to 24.

2. The biocompatible magnetic nanocrystal as claimed in claim 1, wherein said biocompatible magnetic nanocrystal is a paramagnetic, superparamagnetic or ferromagnetic nanometer-sized crystal.

3. The biocompatible magnetic nanocrystal as claimed in claim 1, wherein said biocompatible magnetic nanocrystal is selected from a group consisting of a magnetic transition metal or an oxide thereof, a magnetic lanthanide oxide, a transition metal- or lanthanide-doped magnetic metal oxide, and the particle size of said nanocrystal ranges from 1 to 60 nm.

4. The biocompatible magnetic nanocrystal as claimed in claim 1, wherein said biocompatible macromolecule is selected from polyethylene glycol or a block copolymer having a polyethylene glycol segment, said macromolecule having a molecular weight of 600 to 20000 and bearing one or more carboxyl groups or amino groups.

5. The biocompatible magnetic nanocrystal as claimed in claim 4, wherein said biocompatible macromolecule is selected from a linear or branched poly(ethylene glycol), and a block copolymer consisting of a linear or branched poly (ethylene glycol) segment and a poly(acrylic acid), poly (methacrylic acid), poly(ethyleneimine), polyalanine, polylysine, polyleucine, poly(glutamic acid), poly(aspartic acid), polycaprolactone or poly(lactic acid) segment.

6. The biocompatible magnetic nanocrystal as claimed in claim 1, wherein said biocompatible macromolecule bonded on the surface of said magnetic nanocrystal further offer one or more carboxyl groups or amino groups for further covalently conjugating the magnetic nanocrystal to a biomolecule.

7. The biocompatible magnetic nanocrystal as claimed in claim 1, wherein the weight percentage of said biocompatible macromolecule in said biocompatible magnetic nanocrystal ranges from 5% to 80%.

8. A method for preparing the biocompatible magnetic nanocrystal as claimed in claim 1, wherein the reaction is a one-pot reaction comprising:
    introducing a precursor of magnetic nanocrystal, a biocompatible macromolecule, and an alkyl-containing molecule into a non-polar or weak-polar high boiling-point solvent; purging the reaction solution with an inert gas to remove oxygen; and then heating the resultant solution to directly obtain a biocompatible magnetic nanocrystal, wherein:
    the precursor of magnetic nanocrystal is a metal-organic coordination compound or a metal-inorganic compound comprising transition metal ion or rare-earth metal ion with a concentration of 0.001 to 0.2 mol/L, the biocompatible macromolecule is polyethylene glycol or a block copolymer having a polyethylene glycol segment, said biocompatible macromolecule having a molecular weight of 600 to 20000 and bearing one or more carboxyl groups or amino groups, and the concentration thereof ranging from 0.001 mol/L to 1 mol/L, the alkyl-containing molecule is chosen from an alkyl amine, an alkyl carboxylic acid or an alkyl alcohol with a concentration of 0 to 0.2 mol/L, and the number of $CH_2$ units in said alkyl-containing molecule ranging from 4 to 24.

9. The method as claimed in claim 8, wherein said transition metal or rare-earth metal in said precursor is chosen from iron, cobalt, nickel, manganese and lanthanide.

10. The method as claimed in claim 8, wherein said metal-organic coordination compound is formed by a transition metal or rare-earth metal ion with an organic ligand comprising acetylacetonate, carbonyl, phenyl acetylacetonate, cyclopentadienyl, and N-nitrosophenylhydroxylamine.

11. The method as claimed in claim 8, wherein said precursor of magnetic nanocrystal is selected from the group consisting of oleate, stearate, acetate, gluconate, citrate, oxalate, chloride, sulfate, nitrate, and fatty acid salts of a transition metal or rare-earth metal ion, and hydrates of these salts.

12. The method as claimed in claim 8, wherein said nonpolar or weak-polar high boiling-point solvent has a boiling-point above 160° C.

13. The method as claimed in claim 8, further comprising:
using an organic solvent to precipitate and subsequently wash the biocompatible magnetic nanocrystal, and then collecting said biocompatible magnetic nanocrystal via centrifugation; and purifying the biocompatible magnetic nanocrystal dissolved in deionized water by dialysis, thereby obtaining a solution of said biocompatible magnetic nanocrystal.

14. The method as claimed in claim 13, further comprising:
converting said biocompatible magnetic nanocrystal solution to a nanocrystal powder via procedures including precipitating, washing, and drying processes.

* * * * *